United States Patent
Nagarajan et al.

(10) Patent No.: US 11,440,937 B2
(45) Date of Patent: Sep. 13, 2022

(54) CHROMATOGRAPHY PROCESS FOR PURIFICATION OF INSULIN ANALOGUES

(71) Applicant: BIOCON BIOLOGICS LIMITED, Karnataka (IN)

(72) Inventors: Ramprabu Nagarajan, Karnataka (IN); Minal Hashim, Karnataka (IN); Azimoddin Minyasab Shaikh, Karnataka (IN); Sandhya Hedge, Karnataka (IN); Partha Hazra, Karnataka (IN)

(73) Assignee: BIOCON BIOLOGICS LIMITED

( * ) Notice: Subject to any disclaimer, the term of this patent is extended or adjusted under 35 U.S.C. 154(b) by 6 days.

(21) Appl. No.: 17/266,666

(22) PCT Filed: Aug. 20, 2019

(86) PCT No.: PCT/IB2019/056998
§ 371 (c)(1),
(2) Date: Feb. 8, 2021

(87) PCT Pub. No.: WO2020/039339
PCT Pub. Date: Feb. 27, 2020

(65) Prior Publication Data
US 2021/0355158 A1 Nov. 18, 2021

(30) Foreign Application Priority Data
Aug. 20, 2018 (IN) .............................. 201841031091

(51) Int. Cl.
*C07K 1/20* (2006.01)
*C07K 14/62* (2006.01)

(52) U.S. Cl.
CPC ................ *C07K 1/20* (2013.01); *C07K 14/62* (2013.01)

(58) Field of Classification Search
CPC .................................. A61K 1/20; A61K 14/62
See application file for complete search history.

(56) References Cited

U.S. PATENT DOCUMENTS

| 6,180,757 | B1 | 1/2001 | Bogsnes |
| 6,800,606 | B1 | 10/2004 | You-Min et al. |
| 8,802,816 | B2 | 8/2014 | Haza |
| 2012/0178900 | A1 | 7/2012 | Dave et al. |
| 2017/0174737 | A1 | 6/2017 | Watson |

FOREIGN PATENT DOCUMENTS

| CN | 108218954 A | 6/2018 |
| WO | WO1999/52934 A1 | 10/1999 |
| WO | WO2009/104199 A1 | 8/2009 |
| WO | WO2011/018745 | 2/2011 |

OTHER PUBLICATIONS

The Handbook of Analysis and Purification of Peptides and Protein by Reversed Phase HPLC GRACEVDAC, third ED. 2002.
Eugene P. Kroeff et al. 1989 Production scale purification of biosynthetic human insulin by reversed-phase high performance liquid chromatography, Journal of Chromatography, V. 461, pp. 45-61.
Hart G. W, Glycosylation, Curr. Opin. Cell. Biol 1992; 4: 1017.
Gemmill T R et al., Overview of N- and O-linked oligosaccharide structures found in various yeast species, Biochemica et Biophysica Acta, 1999; 1426:227.
Walsh G, Biopharmaceutical benchmarks 2006, Nature Biotechnology, 2006; 24:769.
Chung, P-L et al. A parallel pore and surface diffusion model for predicting the adsorption and elution profiles of lispro insulin and two impurities in gradient-elution reversed phase chromatography, Journal of Chromatography, 2010, 1217:8103-8120.
European Search Report, corresponding to European Patent Application No. 19853094.1, issued by the European Patent Office dated Mar. 30, 2022.
Guan, X. et al. Chemically Precise Glycoengineeiing Improves Human Insulin, ACS Chem Biol., 2018, 13(1):73-81.
Heinemann, L. et al. Biosimilar Insulins: Basic Considerations, Journal of Diabetes Science and Technology, 2014, 8(1):6-13.
Kannan, V. et al. A tandem mass spectrometric approach to the identification of O-glycosylated glargine glycoforms in active pharmaceutical ingredient expressed in *Pichia pastoris*, Rapid Commun. Mass Spectrom., 2009, 23:1035-1042.
Szewczak, J. et al. Isolation and Characterization of Acetylated Derivative of Recombinant Insulin Lispro Produced in *Escherichia coli*, Pharm Res, 2015, 32:2450-2457.

*Primary Examiner* — Jeanette M Lieb
(74) *Attorney, Agent, or Firm* — Marianne Fuierer; Casimir Jones, S.C.

(57) ABSTRACT

The present invention relates to a process for purification of non-glycosylated insulin analogues 5 from a mixture comprising glycosylated and non-glycosylated proteins by removal of glycosylated proteins. The removal is achieved by combination of two RP-HPLC steps.

20 Claims, 16 Drawing Sheets

UV and TIC chromatogram Reverse phase purification-1 end

UV and TIC chromatogram Reverse phase purification-1 end

UV and TIC chromatogram Reverse phase purification-2 end

UV and TIC chromatogram Reverse phase purification-2 end

UV and TIC chromatogram Reverse phase purification-2 end

UV and TIC chromatogram Reverse phase purification-2 end

CHROMATOGRAPHY PROCESS FOR PURIFICATION OF INSULIN ANALOGUES

CROSS-REFERENCE TO RELATED APPLICATIONS

This application is filed under the provisions of 35 U.S.C. § 371 and claims the priority of International Patent Application No. PCT/IB2019/056998 filed on Aug. 20, 2019 which in turn claims priority to Indian Application No. 20184103, filed on Aug. 20, 2018, the contents of all is hereby incorporated by reference herein for all purposes.

The present invention generally relates to the field of protein purification methods. In particular, there is provided a chromatographic process for purification of non-glycosylated insulin analogue.

BACKGROUND OF INVENTION

Recombinant forms of insulin, insulin analogues and/or derivatives have been produced in various microbial expression systems. Organisms such as *E. coli, S. cerevisiae* have been employed for the commercial production of recombinant human insulin and derivatives thereof. Proteins or protein precursors may originate from yeast expression systems, correlation between a high expression level and an increase in glycosylated protein precursors has been observed. Consequently, the need for a more efficient process of separating the non-glycosylated proteins from the glycosylated proteins has become even more apparent. Owing to the disadvantages of these systems such as low expression levels, difficulties in downstream purification etc., the use of methylotrophic yeast *Pichia pastoris* has been favoured as a protein expression system. In U.S. Pat. No. 6,800,606 several advantages of the *Pichia pastoris* expression system have been mentioned such as high expression, low production cost, and high-density culture.

However, one of the major disadvantages of *Pichia pastoris* expression system is the post-translational modification of the recombinant proteins, which exist as impurities in the final product which is very challenging to purify. Although there are a number of post-translational modifications of proteins known, the most common form of post-translational modification is glycosylation (Hart G. W, Glycosylation, Curr. Opin. Cell. Biol 1992; 4: 1017). Glycosylation can be either N-linked or O-linked depending on the expression system (Gemmill T R et al., Overview of N- and O-linked oligosaccharide structures found in various yeast species, Biochemica et Biophysica Acta, 1999; 1426:227). Glycosylation affects stability of protein conformation, immunogenicity, clearance rate, protection from proteolysis and improves protein solubility (Walsh G, Biopharmaceutical benchmarks 2006, Nature Biotechnology, 2006; 24:769).

U.S. Pat. No. 6,180,757 relates to the process of chromatographically separating glycosylated proteins or protein precursors from non-glycosylated proteins or protein precursors using a calcium (Ca++) containing eluent. By using this process a fraction comprising non-glycosylated proteins substantially free from glycosylated proteins is obtained. The patent however, does not disclose completely purified product.

U.S. Pat. No. 8,802,816 by Biocon Limited relates to methods of separation and/or purification of product from impurities yielding a purified heterologous recombinant insulin glargine with 96% purity.

U.S. Pat Publication No. 20120178900 by Biocon Limited discloses RP-HPLC process for purification of insulin Aspart, Atisoban, insulin Glargine and insulin Lispro. The process comprises employing RP-HPLC with an ion paring agent in combination with organic modifier.

OBJECT OF THE INVENTION

The objective of the present invention is to provide a process to obtain at least 99.95% purified non-glycosylated insulin Glargine, and non-glycosylated insulin Lispro which are substantially free of mono-, di- or tri-glycosylated variants. This is achieved by the use of a combination of two reversed phase HPLC steps, where the first step is performed using octane sulphonic acid (OSA) as a preferable ion pairing agent at lower pH and the second step is performed at high pH using sodium perchlorate or Tetra butyl ammonium bisulphate (TBAB) as preferable ion pairing agent. The first and the second step may be performed in the opposite sequence to obtain at least 99.95% removal of glycosylated variants of insulin Glargine or insulin Lispro.

SUMMARY OF THE INVENTION

The present invention relates to a process for purification of non-glycosylated insulin analogue(s) such as insulin Glargine and insulin Lispro from a complex mixture comprising non-glycosylated, mono-, and poly-glycosylated variants of Insulin Lispro and Glargine by achieving at least 99.95% removal of said glycosylated variants.

The purification process comprises two steps of Reverse Phase—High Performance Liquid Chromatography (RP-HPLC) that are performed consecutively. In one possible method, the first step RP-HPLC is performed with the said complex mixture in the presence of an ion pairing agent preferably octane sulphonic acid (OSA) in combination with an organic modifier preferably acetonitrile in an acidic pH to yield a first mixture comprising partially purified non-glycosylated insulin analogue with significantly reduced levels of glycosylated variants of insulin analogue. The second step RP-HPLC is performed with the first mixture at basic pH in combination with an ion pairing agent and an organic modifier preferably acetonitrile to yield at least 99.95% purified non-glycosylated insulin analogue.

In a second possible method, the first step RP-HPLC is performed with the said complex mixture at a basic pH in combination with an ion pairing agent and an organic modifier preferably acetonitrile to yield a first mixture comprising partially purified non-glycosylated insulin analogue with significantly reduced levels of glycosylated variants of insulin analogue. The second step RP-HPLC is performed with the first mixture at acidic pH in the presence of an ion pairing agent preferably octane sulphonic acid (OSA) in combination with an organic modifier, preferably acetonitrile to yield at least 99.95% purified non-glycosylated insulin analogue.

The insulin analogue can be insulin Glargine, or insulin Lispro. The ion pairing agent used in RP-HPLC under basic pH conditions is preferably sodium perchlorate when the insulin analogue is insulin Glargine. The ion pairing agent used in RP-HPLC under basic pH conditions is preferably TBAB when the insulin analogue is insulin Lispro.

The removal of glycosylated forms of insulin analogue is achieved by the combination of low pH based RP-HPLC and high pH based RP-HPLC. As a result, at least 99.95% of glycosylated variants of insulin Glargine and insulin Lispro are removed.

This summary is not intended to identify essential features of the claimed subject matter nor is it intended for use in determining or limiting the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

Figure 7A:
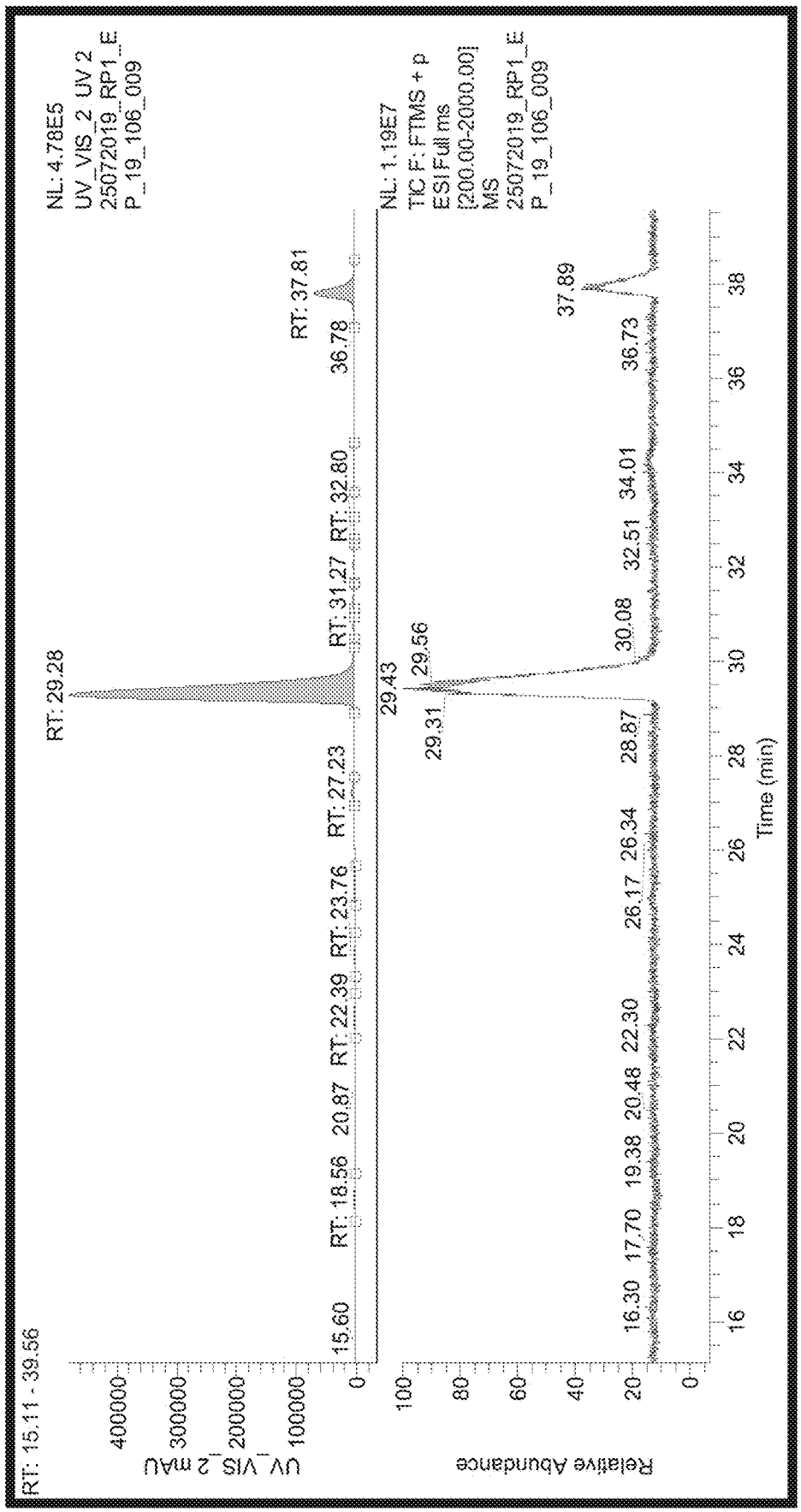
Figure 7B:
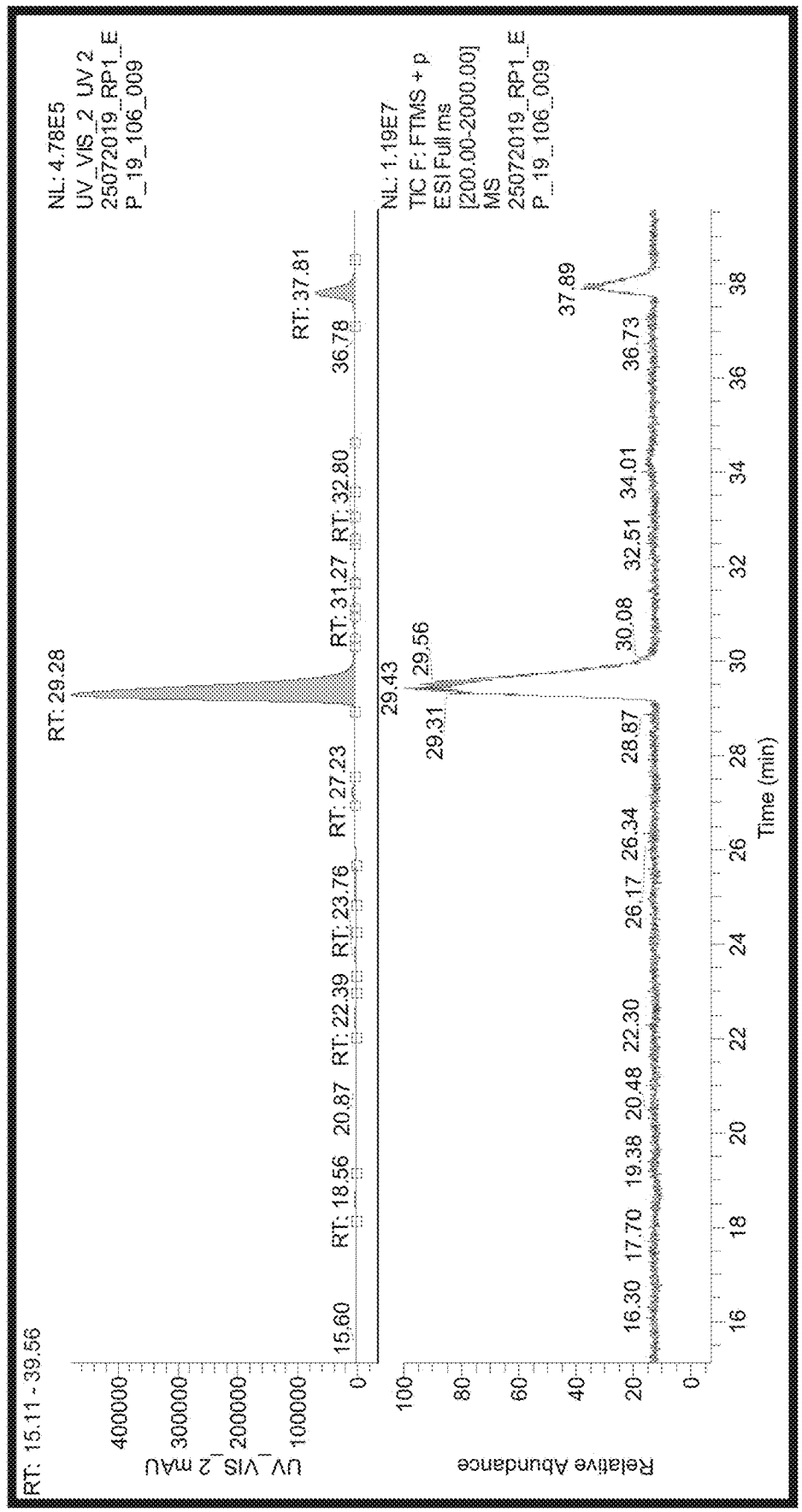
Figure 7C:
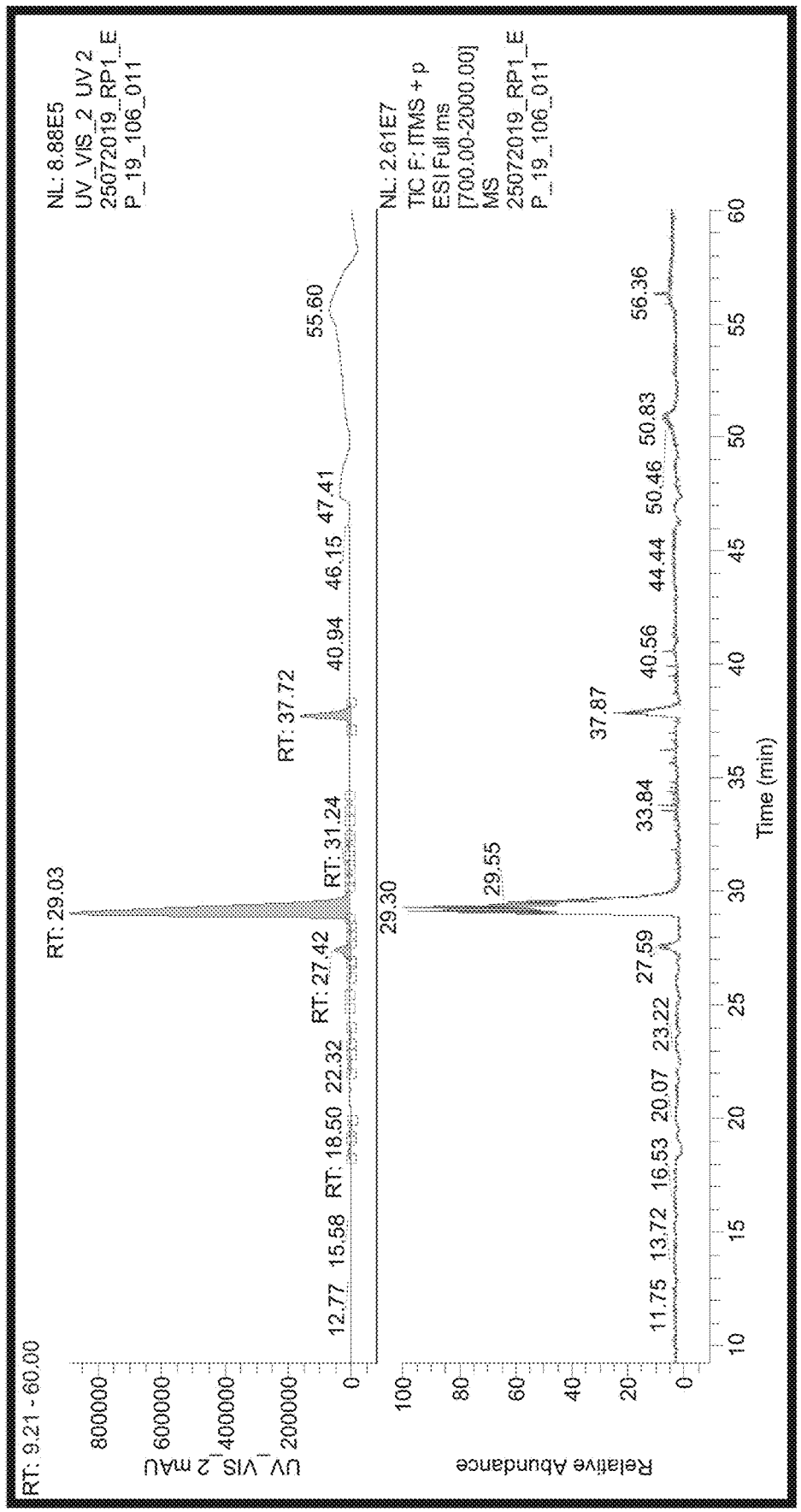

FIG. 7A, 7B, 7C UV and TIC chromatogram Reverse phase purification-1 end of process of purification of insulin Lispro with high pH followed by low pH chromatography.

Figure 8A:
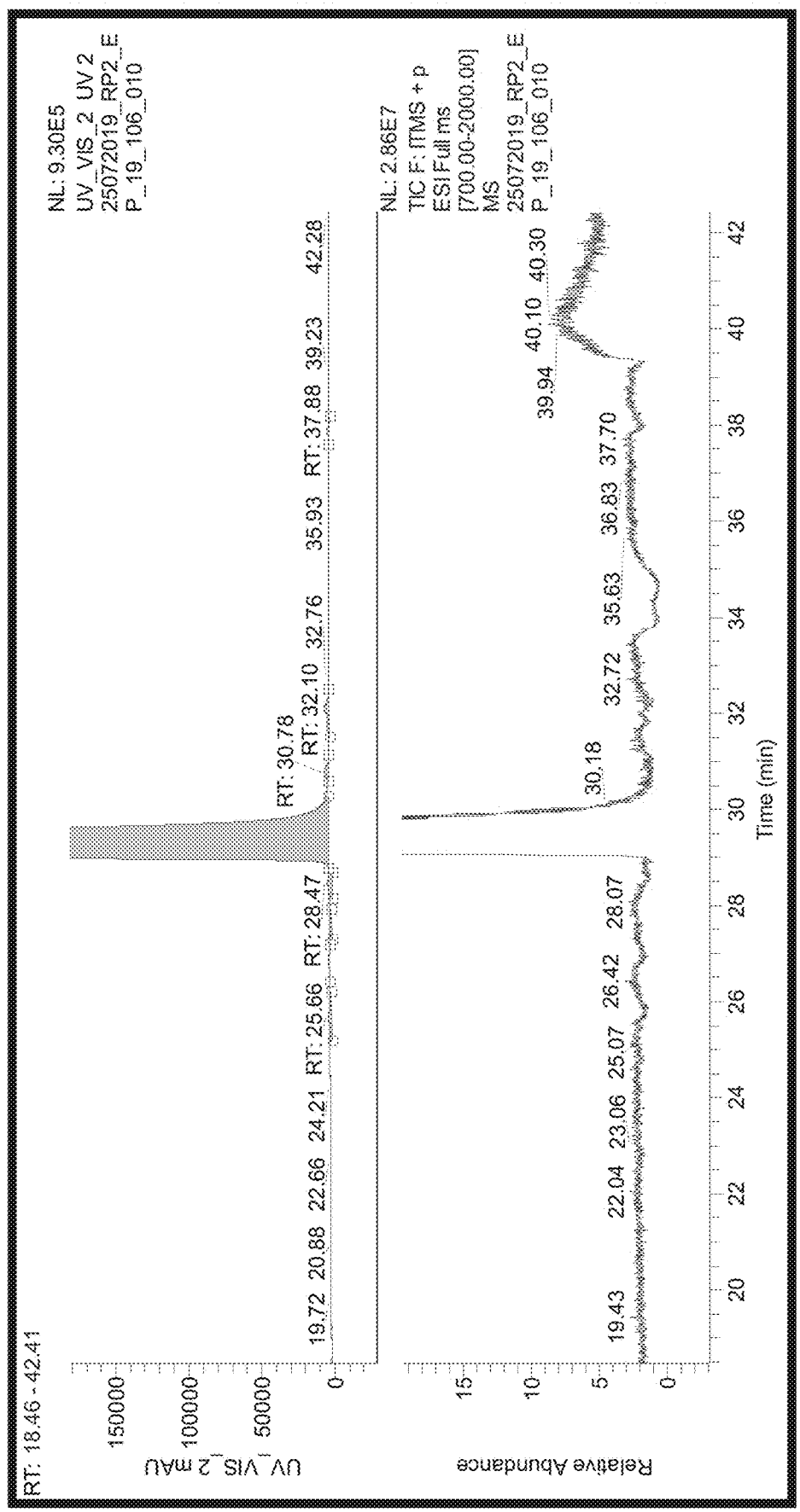
Figure 8B:
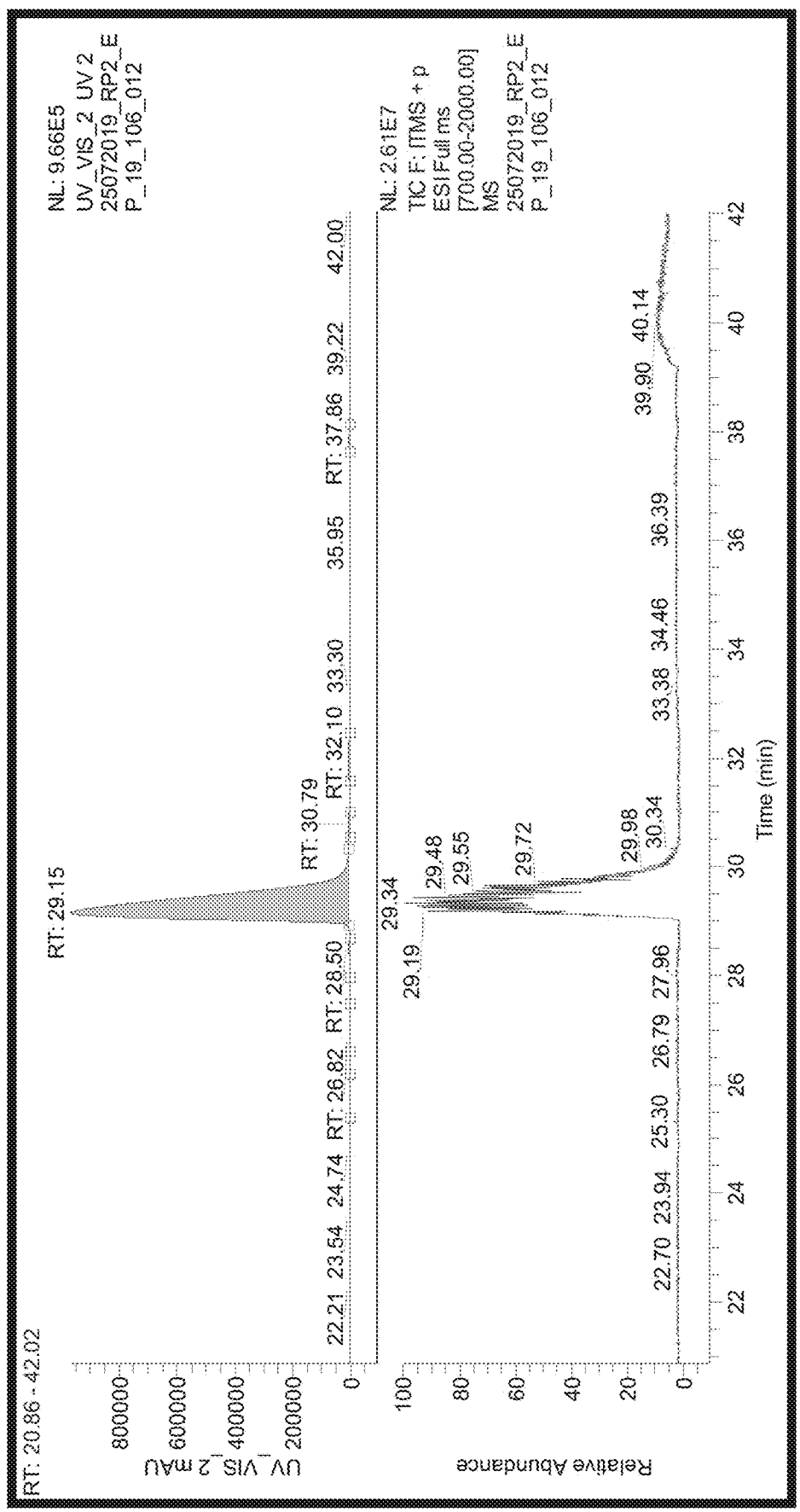
Figure 8C:
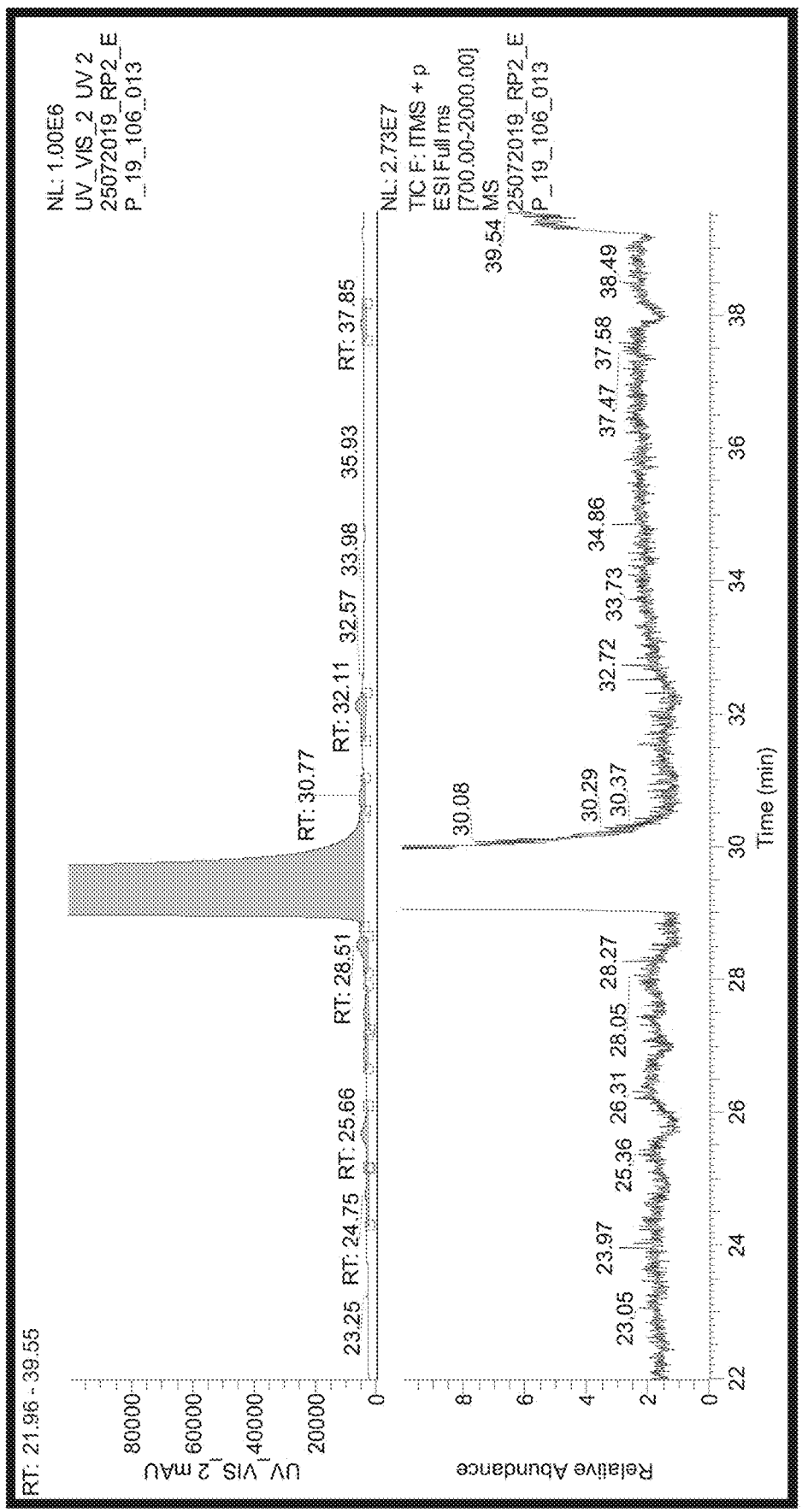

FIG. 8A, 8B, 8C UV and TIC chromatogram Reverse phase purification-2 end of process of purification of insulin Lispro with high pH followed by low pH chromatography.

DETAILED DESCRIPTION OF INVENTION

Those skilled in the art will be aware that the invention described herein is subject to variations and modifications other than those specifically described. It is to be understood that the invention described herein includes all such variations and modifications. The invention also includes all such steps, features, compositions and methods referred to or indicated in this specification, individually or collectively, and any and all combinations of any two or more of said steps or features.

Definitions

For convenience, before further description of the present invention, certain terms employed in the specification, examples are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The present disclosure is not to be limited in scope by the specific embodiments described herein, which are intended for the purposes of exemplification only.

Functionally-equivalent processes and methods are clearly within the scope of the disclosure, as described herein.

The term "de-glycosylated" particularly refers to proteins wherein the sugar entity (glycans) has been removed from the glycoprotein by purification process.

The term "glycosylated" particularly refers to a protein in which a carbohydrate moiety such as mannose, poly mannose, and ribose sugars are attached to amino acids of A chain or B chain or in both A and B chain of the protein. The term "glycosylated proteins" includes mono-glycosylated proteins as well as poly-glycosylated proteins.

The term "non-glycosylated" particularly refers to the proteins wherein no sugar moieties (glycans) are attached to the any chain of the protein.

The term "Glargine" particularly refers to the rapid-acting and long-acting human insulin analogue which differs from human insulin in that the amino acid Asparagine at position 21 on the Insulin A-chain is replaced by glycine and two Arginine are added to the C-terminus of the B chain.

The term "Lispro" particularly refer to rapid-acting human insulin analogue, which chemically differs from human insulin. In insulin Lispro the amino acid proline at position B28 is replaced by lysine and the lysine in position B29 is replaced by proline.

The term "RP-HPLC" particularly refers to reversed-phase high-performance liquid chromatography, which involves the separation of molecules based on hydrophobicity.

The term "downstream purification" refers to the recovery and purification of biosynthetic pharmaceutical products from related impurities and wastes incurred during the production. The present invention relates to the process of purification of non-glycosylated insulin analogues by at least 99.95% removal of multiple forms of mono-glycosylated and poly-glycosylated insulin analogues. The said process is a selective purification of the product through optimized downstream purification techniques attributed to the better understanding of the nature of impurities present in the final product.

The purification process of purification of non-glycosylated insulin analogues as a result of the combinational impact of two chromatographic techniques employed in succession referred to as purification step-1 and purification step-2. Both the chromatography steps used for the purification of non-glycosylated insulin analogues are column chromatography method, preferably RP-HPLC, or hydrophobic interaction chromatography. The advantage of using aforesaid chromatography is the increased purity of the fractions of non-glycosylated insulin analogues. The purified end product is substantially (at least 99.95%) free of glycosylated variants. Preferably, the concentration of glycosylated forms of insulin analogue in the purified fraction of non-glycosylated insulin is less than 0.05%; thus, removing glycosylated variants to level below quantification (BLOQ).

The present invention further relates to the identification of various glycoforms of insulin analogues, particularly Insulin Glargine and Insulin Lispro through chemical methods coupled with mass spectrometry techniques such as electrospray and matrix assisted laser desorption ionization for identification.

In the present invention, purification step performed at low pH uses octane sulphonic acid as preferred ion pairing agent, preferably sodium salt of octane sulphonic acid (OSA) in the reverse phase mode of chromatography. OSA is a cationic ion pairing agent with an 8-carbon long hydrophobic chain attached to a sulphonic group (S03-). OSA interacts with the protein sample in acidic pH and alters the binding chemistry to yield enhanced resolution between the glycosylated and non-glycosylated proteins.

The current invention has proved to be especially advantageous in the separation of glycosylated insulin from non-glycosylated insulin. Preferably, the concentration of glycosylated insulin in the fraction of purified non-glycosylated insulin is less than 0.05%.

The disclosure will now be illustrated with working examples, which is intended to illustrate the working of disclosure and not intended to take restrictively to imply any limitations on the scope of the present disclosure.

In an embodiment of the present invention, there is provided a process of purification of non-glycosylated insulin analogues from a mixture comprising non-glycosylated and glycosylated insulin analogues.

In an embodiment, the insulin analogue is insulin Glargine. In another embodiment, the insulin analogue is insulin Lispro.

In an embodiment, glycosylated insulin analogues can be mono-glycosylated, di-glycosylated, tri-glycosylated, poly-glycosylated, and mixtures thereof.

In an embodiment, the purification process of the present invention results in at least 99.95% removal of glycosylated forms of insulin analogue from a mixture comprising non-glycosylated and glycosylated insulin analogue. In a preferred embodiment, the removal percentage is 99.96, 99.97, 99.98, 99.99, and 100.

In an embodiment, the purification process of the present invention results in isolation of non-glycosylated insulin Glargine with <0.05% of glycosylated insulin Glargine. In a preferred embodiment, the purification process of the present invention results in isolation of non-glycosylated insulin Glargine with <0.05%, 0.04%, 0.03%, 0.02%, 0.01%, or 0% of glycosylated insulin Glargine.

In an embodiment, the purification process of the present invention results in isolation of non-glycosylated insulin Lispro with <0.05% of glycosylated insulin Lispro. In a preferred embodiment, the purification process of the present invention results in isolation of non-glycosylated insulin Lispro with <0.05%, 0.04%, 0.03%, 0.02%, 0.01%, or 0% of glycosylated insulin Lispro.

In an embodiment, there is provided a process of purification of non-glycosylated insulin Glargine from a mixture comprising non-glycosylated and glycosylated insulin Glargine, said method consisting of a first and a second step, wherein the first step comprises performing RP-HPLC on a mixture comprising glycosylated and non-glycosylated insulin Glargine in the presence of an ion pairing agent and acetonitrile (organic modifier) at an acidic pH to yield a first mixture comprising partially purified non-glycosylated insulin Glargine; wherein the second step comprises performing RP-HPLC on the first mixture from first step in the presence of an ion pairing agent and acetonitrile (organic modifier) at an alkaline pH to yield at least 99.95% pure non-glycosylated insulin Glargine. In a preferred embodiment, the ion pairing agent in the first step is octane sulphonic acid, more preferably sodium salt of OSA, and the ion pairing agent in the second step is sodium perchlorate. In an embodiment, the pH range in the first step is in the range of 3.5-3.9 and the pH range in the second step is in the range of 8.3-8.7.

In an embodiment, there is provided a process of purification of non-glycosylated insulin Lispro from a mixture comprising non-glycosylated and glycosylated insulin Lispro, said method consisting of a first and a second step, wherein the first step comprises performing RP-HPLC on a mixture comprising glycosylated and non-glycosylated insulin Lispro in the presence of an ion pairing agent and acetonitrile (organic modifier) at an acidic pH to yield a first mixture comprising partially purified non-glycosylated insulin Lispro; wherein the second step comprises performing RP-HPLC on the first mixture from first step in the presence of an ion pairing agent and acetonitrile (organic modifier) at an alkaline pH to yield at least 99.95% pure non-glycosylated insulin Lispro. In a preferred embodiment, the ion pairing agent in the first step is octane sulphonic acid, more preferably sodium salt of OSA, and the ion pairing agent in the second step is TBAB. In an embodiment, the pH range in the first step is in the range of 3.5-3.9 and the pH range in the second step is in the range of 8.3-8.7.

In an embodiment, there is provided a process of purification of non-glycosylated insulin Glargine from a mixture comprising non-glycosylated and glycosylated insulin Glargine, said method consisting of a first and a second step, wherein the first step comprises performing RP-HPLC on a mixture comprising glycosylated and non-glycosylated insulin Glargine in the presence of an ion pairing agent and acetonitrile (organic modifier) at an alkaline pH to yield a first mixture comprising partially purified non-glycosylated insulin Glargine; wherein the second step comprises performing RP-HPLC on the first mixture from first step in the presence of an ion pairing agent and acetonitrile (organic modifier) at an acidic pH to yield at least 99.95% pure non-glycosylated insulin Glargine. In a preferred embodiment, the ion pairing agent in the first step is sodium perchlorate, and the ion pairing agent in the second step is octane sulphonic acid, preferably sodium salt of octane sulphonic acid. In an embodiment, the pH range in the first step is in the range of 8.3-8.7 and the pH range in the second step is in the range of 3.5-3.9. In an embodiment, there is provided a process of purification of non-glycosylated insulin Lispro from a mixture comprising non-glycosylated and glycosylated insulin Lispro, said method consisting of a first and a second step, wherein the first step comprises performing RP-HPLC on a mixture comprising glycosylated and non-glycosylated insulin Lispro in the presence of an ion pairing agent and acetonitrile (organic modifier) at an alkaline pH to yield a first mixture comprising partially purified non-glycosylated insulin Lispro; wherein the second step comprises performing RP-HPLC on the first mixture from first step in the presence of an ion pairing agent and acetonitrile (organic modifier) at an acidic pH to yield at least 99.95% pure non-glycosylated insulin Lispro. In a preferred embodiment, the ion pairing agent in the first step is TBAB, and the ion pairing agent in the second step is octane sulphonic acid, preferably sodium salt of octane sulphonic acid. In an embodiment, the pH range in the first step is in the range of 8.3-8.7 and the pH range in the second step is in the range of 3.5-3.9.

In an embodiment, there is provided non-glycosylated insulin Glargine at least 99.95% free of glycosylated variants of insulin Glargine. In an embodiment, there is provided non-glycosylated insulin Glargine at least 99.96% free of glycosylated variants of insulin Glargine. In an embodiment, there is provided non-glycosylated insulin Glargine at least 99.97% free of glycosylated variants of insulin Glargine. In an embodiment, there is provided non-glycosylated insulin Glargine at least 99.98% free of glycosylated variants of insulin Glargine. In an embodiment, there is provided non-glycosylated insulin Glargine at least 99.99% free of glycosylated variants of insulin Glargine. In an embodiment, there is provided non-glycosylated insulin Glargine 100% free of glycosylated variants of insulin Glargine.

In an embodiment, there is provided non-glycosylated insulin Lispro at least 99.95% free of glycosylated variants of insulin Lispro. In an embodiment, there is provided non-glycosylated insulin Lispro at least 99.96% free of glycosylated variants of insulin Lispro. In an embodiment, there is provided non-glycosylated insulin Lispro at least 99.97% free of glycosylated variants of insulin Lispro. In an embodiment, there is provided non-glycosylated insulin Lispro at least 99.98% free of glycosylated variants of insulin Lispro. In an embodiment, there is provided non-glycosylated insulin Lispro at least 99.99% free of glycosylated variants of insulin Lispro. In an embodiment, there is provided non-glycosylated insulin Lispro 100% free of glycosylated variants of insulin Lispro.

Examples

Figure 1:
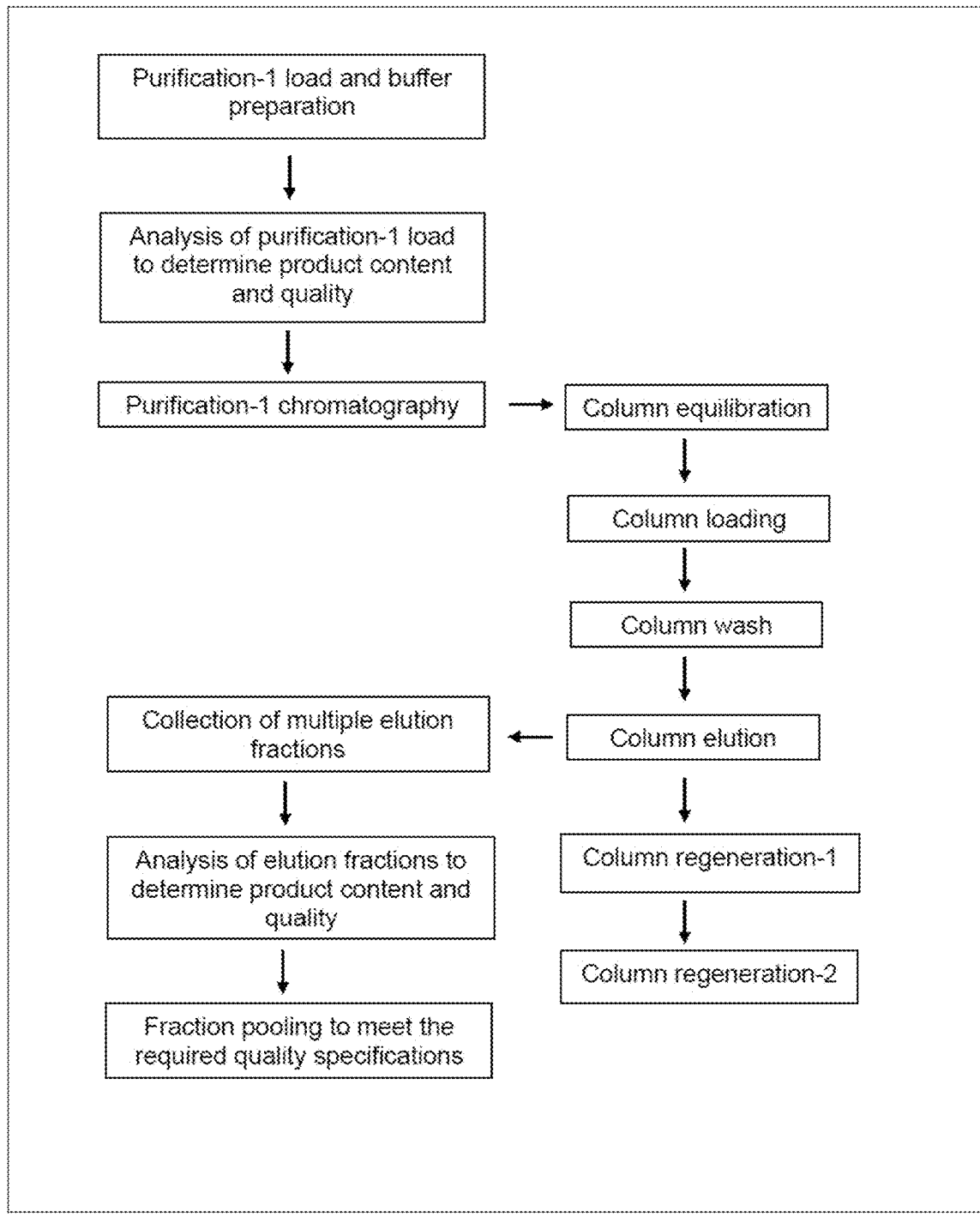
FIG. 1 represents flow chart of process of purification step-1.

Purification of Insulin Glargine Wherein Low pH Based RP-HPLC is Followed by High pH Based RP-HPLC The Purification step-1 at low pH is as shown in flowchart of FIG. 1. The details of purification step-1 are as follows
Stationary Phase Details:
  a. Media: Kromasil C8-100A-13 pm
  b. Height: 25. Oil. 0cm
  c. Linear velocity: <360 cm/h for all the chromatographic steps Mobile phase details:
  a. Mobile phase A: 100 mM Sodium acetate+0.05% (w/v) Octane sulphonic acid (OSA) at pH 3.7±0.1 (pH is adjusted using Glacial acetic acid)
  b. Mobile phase B: 100.0% Acetonitrile
  c. Mobile phase A& B temperature during purification cycle: 20-30° C.

Load preparation:
  a. Load concentrate obtained from the preceding step was diluted with a mixture of purified water and acetic acid at the ratio of >1.0:10.0.
  b. After dilution, the sample was filtered through 1.2 pm, 0.45 pm followed by 0.22 pm filters.
  c. Filters used for 1.2 pm filtration was made of polypropylene (PP) & for 0.45/0.22 pm filtration was made of polyether sulfone (PES) material.
  d. The product concentration in the load was expected to be in the range of 1.0 to 2.0 g/L.

Process conditions for purification:
  a. The column was equilibrated for 4-5 CVs (column volumes) using mobile phase of 90.0% (A):10.0% (B) at linear velocity of <360 cm/h.
  b. The column was loaded at a capacity of 4-12 g glargine/L of Kromasil at linear velocity of <360 cm/h.
  c. After loading, the column was washed for 4-5 CVs (column volumes) using mobile phase of 85.0% (A): 15.0% (B) at linear velocity of <360 cm/h.
  d. The product was eluted out from the column using linear gradient of 24-31% B over 25 CVs at linear velocity of <360 cm/h.
  e. During elution, variable volume fraction collection was performed based on rise in absorbance (UV) at 280 nm. The collection was continued till UV2 so drops to baseline. The volume required to elute the protein from the column was 2.0-3.0 CVs.
  f. The elution fractions were analyzed pooled based on their purity levels and the prepared elution pool was stored at 2-8° C.
  g. After elution to remove the residual protein if any, the column was regenerated for 2 CVs in the up-flow direction using 50.0% 1M acetic acid & 50.0% acetonitrile, followed by 1 CV using 30.0% 1M acetic acid & 70.0% acetonitrile at linear velocity of <360 cm/h.

Results at different relative retention time (RRT) were as per the tabulated data in table 1. According to data, the glycosylated proteins were reduced by ~4.5 folds i.e. from "'2.6% in the load to ~0.6% in the elution pool (EP).

TABLE 1

Results of Purification step-1 at low pH

| Trial No. | Stage | % Purity of insulin glargine 1.00 RRT | % Purity of glycosylated insulin glargine | | | | | % Recovery |
|---|---|---|---|---|---|---|---|---|
| | | | 0.78-0.81 RRT | 0.82-0.84 RRT | 0.94 RRT | 0.96-0.97 RRT | 0.98-0.99 RRT | |
| 1. | Load | 61.23 | 0.52 | 0.65 | 0.25 | 0.68 | 0.58 | 81.2 |
| | EP | 97.90 | BLOD | 0.19 | BLOD | 0.17 | 0.13 | |
| 2. | Load | 60.91 | 0.51 | 0.76 | 0.30 | 0.63 | 0.69 | 84.7 |
| | EP | 98.00 | BLOD | 0.40 | BLOD | 0.16 | 0.07 | |
| 3. | Load | 62.47 | 0.32 | 0.66 | 0.23 | 0.61 | 0.62 | 83.4 |
| | EP | 97.46 | BLOD | 0.30 | BLOD | 0.16 | 0.12 | |

Note:
LOQ (limit of quantitation) for the analytical method is 0.04% and LOD (limit of detection) is 0.02%, BL OD-below limit of detection.

The elution pool from purification step-1 was subjected to purification step-2 for further purification of the non-glycosylated proteins from the glycosylated proteins.

Figure 2:
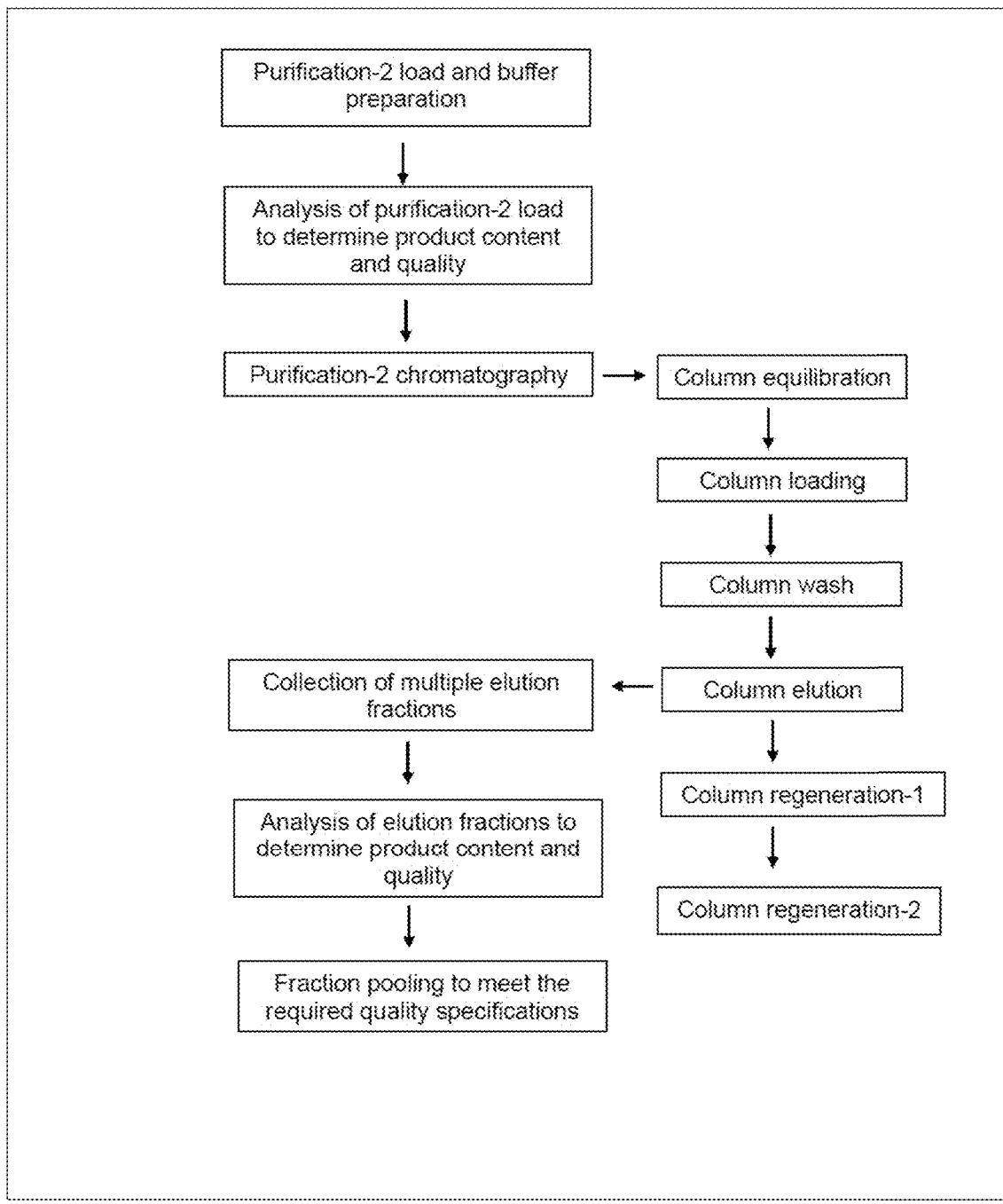
FIG. 2 represents flow chart of process of purification step-2.

The Purification step-2 at high pH were as shown in flowchart of FIG. 2. The details of purification step-2 were as follows
Stationary phase details:
  a. Media: Kromasil C8-100A-13 pm
  b. Height: 25. Oil. 0 cm
  c. Linear velocity: <360 cm/h for all the chromatographic steps Mobile phase details:
  a. Mobile phase A: 100 mM Tris+50 mM Sodium perchlorate at pH 8.5±0.1 (pH is adjusted using Glacial acetic acid)
  b. Mobile phase B: 100.0% Acetonitrile
  c. Mobile phase A& B temperature during purification cycle: 20-30° C.

Load preparation:
  a. Elution pool (EP) obtained from purification step-1 was diluted with purified water at the ratio of 1.0:2.0.
  b. Diluted sample pH was adjusted to 8.5±0.1 using 2.5M Tris.
  c. After pH adjustment the sample was filtered through 1.2 miti, 0.45 pm followed by 0.22 mih.
  d. Filters used for 1.2 miti filtration was made of polypropylene (PP) & for 0.45/0.22 pm filtration was made of polyether sulfone (PES) material.
  e. The product concentration in the load was expected to be in the range of 1.0 to 2.0 g/L.

Process conditions for purification:
  a. The column was equilibrated for 4-5 CVs (column volumes) using mobile phase of 90.0% (A):10.0% (B) at linear velocity of <360 cm/h.
  b. The column was loaded at a capacity of 4-12 g glargine/L of Kromasil at linear velocity of <360 cm/h.
  c. After loading, the column was washed for 4-5 CVs (column volumes) using mobile phase of 80.0% (A): 20.0% (B) at linear velocity of <360 cm/h.
  d. The product was eluted out from the column using linear gradient of 25-29% B over 25 CVs at linear velocity of <360 cm/h.
  e. During elution, variable volume fraction collection was performed based on rise in absorbance (UV) at 280 nm. The collection was continued till UV drops to baseline. The volume required to elute the protein from the column was 2.0-3.0 CV.
  f. After fraction collection, the fractions pH was adjusted to 4.0±0.1 using glacial acetic acid. The expected acid acetic consumption was 15.0%-25.0% (V/V).
  g. The elution fractions were analyzed, pooled based on their purity levels and the prepared elution pool was stored at 2-8° C.
  h. After elution to remove the residual protein if any, the column is regenerate for 3 CVs in the up-flow direction using 50.0% purified water & 50.0% acetonitrile at linear velocity of <360 cm/h.

Results were as per the tabulated data in table 2. According to data, the glycosylated proteins were reduced to 0.00% in the elution pool from ~0.5% in the load.

TABLE 2

Results of Purification step-2 at high pH

| Trial No. | Stage | % Purity of Insulin Glargine 1.00 RRT | % Purity of glycosylated insulin glargine | | | | | % Recovery |
|---|---|---|---|---|---|---|---|---|
| | | | 0.78-0.81 RRT | 0.82-0.84 RRT | 0.94 RRT | 0.96-0.97 RRT | 0.98-0.99 RRT | |
| 1. | Load | 97.06 | BLOD | 0.14 | 0.03 | 0.21 | 0.09 | 86.2 |
| | EP | 100.00 | BLOD | BLOD | BLOD | BLOD | BLOD | |
| 2. | Load | 96.72 | 0.03% | 0.20 | 0.00 | 0.09 | 0.07 | 86.2 |
| | EP | 100.00 | BLOD | BLOD | BLOD | BLOD | BLOD | |
| 3. | Load | 95.92 | 0.04 | 0.23 | 0.04 | 0.27 | 0.10 | 87.0 |
| | EP | 100.00 | BLOD | BLOD | BLOD | BLOD | BLOD | |

Note:
LOQ for the analytical method is 0.04% and LOD is 0.02%

A more complete understanding can be obtained by reference to the following examples, which are provided for purposes of illustration only and are not intended to limit the scope of the disclosure.

Example 1 illustrates purification step-1 which is reverse phase purification-1 at low pH via experiment no 1 to 10.

Experiment 1

The enzyme reaction end containing human insulin glargine in the concentration of 40 mg/ml, was adjusted to 5% acetonitrile, 0.5M acetic acid and was diluted to 1.31 mg/ml using purified water, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~8.0 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+ 0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd). The results are tabulated below in table 3.

TABLE 3

Results of Experiment 1

| Loading(g/L) | Stage | % Purity | % Total glycosylated variants | % Recovery |
|---|---|---|---|---|
| 8.09 | Load | 61.74 | 2.16 | 71 |
| | EP | 97.23 | 0.67 | |

Experiment 2

The enzyme reaction end containing human insulin glargine in the concentration of 40 mg/ml, was adjusted to 5% acetonitrile, 0.5M acetic acid and was diluted to 1.37 mg/ml using purified water, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~8.0 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample and elution fractions and elution pool was analyzed by YMC C18 method. The results are tabulated below in table 4.

TABLE 4

Results of Experiment 2

| Loading(g/L) | Stage | % Purity | % Total glycosylated variants | % Recovery |
| --- | --- | --- | --- | --- |
| 8.08 | Load | 61.10 | 1.55 | 69 |
|  | EP | 98.09 | 0.38 |  |

Experiment 3

The enzyme reaction end containing human insulin glargine in the concentration of 40 mg/ml, was adjusted to 5% acetonitrile, 0.5M acetic acid and was diluted to 1.42 mg/ml using purified water, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~7.6 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 5.

TABLE 5

Results of Experiment 3

| Loading(g/L) | Stage | % Purity | % Total glycosylated variants | % Recovery |
| --- | --- | --- | --- | --- |
| 7.65 | Load | 61.80 | 2.47 | 73 |
|  | EP | 97.76 | 0.41 |  |

Experiment 4

The enzyme reaction end containing human insulin glargine in the concentration of 18 mg/ml, was adjusted to 5% acetonitrile, 0.5M acetic acid and was diluted to 1.5 mg/ml using purified water, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~10.0 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 6.

TABLE 6

Results of Experiment 4

| Loading(g/L) | Stage | % Purity | % Total glycosylated variants | % Recovery |
| --- | --- | --- | --- | --- |
| 8.04 | Load | 60.55 | 3.78 | 73 |
|  | EP | 97.50 | 0.54 |  |

Experiment 5

The enzyme reaction end containing human insulin glargine in the concentration of 18 mg/ml, was adjusted to 5% acetonitrile, 0.5M acetic acid and was diluted to 1.6 mg/ml using purified water, to be used as the load sample. A pre-packed, reverse phase Kromasil 100-13-C8 column (2.1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~10 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 7.

TABLE 7

Results of Experiment 5

| Loading(g/L) | Stage | % Purity | % Total glycosylated variants | % Recovery |
| --- | --- | --- | --- | --- |
| 10.1 | Load | 60.45 | 3.08 | 70 |
|  | EP | 97.88 | 0.42 |  |

Experiment 6

The enzyme reaction end containing human insulin glargine in the concentration of 32 mg/ml, was adjusted to 5% acetonitrile, 0.5M acetic acid and was diluted to 1.5 mg/ml using purified water, to be used as the load sample. A pre-packed, reverse phase Kromasil 100-13-C8 column (2.1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~10 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 8.

TABLE 8

Results of Experiment 6

| Loading(g/L) | Stage | % Purity | % Total glycosylated variants | % Recovery |
|---|---|---|---|---|
| 10.44 | Load | 61.48 | 2.91 | 71 |
|  | EP | 96.86 | 0.64 |  |

Experiment 7

The enzyme reaction end containing human insulin glargine in the concentration of 16 mg/ml, was adjusted to 5% acetonitrile, 0.5M acetic acid and was diluted to 1.5 mg/ml using purified water, to be used as the load sample. A pre-packed, reverse phase Kromasil 100-13-C8 column (2.1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~10 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 9.

TABLE 9

Results of Experiment 7

| Loading(g/L) | Stage | % Purity | % Total glycosylated variants | % Recovery |
|---|---|---|---|---|
| 10.0 | Load | 61.52 | 2.45 | 70 |
|  | EP | 97.66 | 0.57 |  |

Experiment 8

The enzyme reaction end containing human insulin glargine in the concentration of 36 mg/ml, was adjusted to 5% acetonitrile, 0.5M acetic acid and was diluted to 1.6 mg/ml using purified water, to be used as the load sample. A Novosep stainless steel column packed with Kromasil 100-13-C8 resin (5*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~9 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 10.

TABLE 10

Results of Experiment 8

| Loading(g/L) | Stage | % Purity | % Total glycosylated variants | % Recovery |
|---|---|---|---|---|
| 8.55 | Load | 61.64 | 2.68 | 74 |
|  | EP | 98.07 | 0.48 |  |

Experiment 9

The enzyme reaction end containing human insulin glargine in the concentration of 32 mg/ml, was adjusted to 5% acetonitrile, 0.5M acetic acid and was diluted to 1.7 mg/ml using purified water, to be used as the load sample. A Novosep stainless steel column packed with Kromasil 100-13-C8 resin (5*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~9 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 25-32% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 11.

TABLE 11

Results of Experiment 9

| Loading(g/L) | Stage | % Purity | % Total glycosylated variants | % Recovery |
|---|---|---|---|---|
| 9.14 | Load | 60.97 | 3.81 | 71 |
|  | EP | 96.98 | 0.70 |  |

Experiment 10

The enzyme reaction end containing human insulin glargine in the concentration of 32 mg/ml, was adjusted to 5% acetonitrile, 0.5M acetic acid and was diluted to 1.7 mg/ml using purified water, to be used as the load sample. A Novosep stainless steel column packed with Kromasil 100-13-C8 resin (5*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~11 g of human insulin glargine/L of resin. The loosely bound protein was washed with 100 mM Sodium Acetate+0.05% OSA buffer at pH 3.7±0.1 and 15% Acetonitrile for around 4 column volumes. The bound protein were eluted at a gradient of 25-32% Acetonitrile with 85% 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 12.

TABLE 12

Results of Experiment 10

| Loading(g/L) | Stage | % Purity | % Total glycosylated variants | % Recovery |
|---|---|---|---|---|
| 11.28 | Load | 60.97 | 3.81 | 74 |
|  | EP | 96.69 | 0.68 |  |

The summary of experimental data of Reverse phase purification-1 at low pH is elaborated below in table 13.

The first reverse phase purification step for human insulin Glargine used low pH buffers coupled with ion pairing agent octane sulphonic acid (OSA) to reduce the glycosylated variants by 68-90%, thereby increasing the purity from ~60% in the load to >97% in the elution pool (EP).

TABLE 13 summary of experimental data of Reverse phase purification-1 at low pH

| Experiment No. | Column dimensions (cm) | Loading (g/L) | Stage | % Purity | % Total glycosylated variants | % Recovery |
|---|---|---|---|---|---|---|
| 1 | 1*25 | 8.09 | Load | 61.74 | 2.16 | 69 |
|  |  |  | EP | 97.23 | 0.67 |  |
| 2 | 1*25 | 8.08 | Load | 61.10 | 1.55 | 71 |
|  |  |  | EP | 98.09 | 0.38 |  |
| 3 | 1*25 | 7.65 | Load | 61.80 | 2.47 | 69 |
|  |  |  | EP | 97.76 | 0.41 |  |
| 4 | 1*25 | 10.01 | Load | 60.55 | 3.78 | 73 |
|  |  |  | EP | 97.50 | 0.54 |  |
| 5 | 2.1*25 | 8.11 | Load | 60.45 | 3.08 | 72 |
|  |  |  | EP | 97.88 | 0.42 |  |
| 6 | 2.1*25 | 10.44 | Load | 61.48 | 2.91 | 68 |
|  |  |  | EP | 96.86 | 0.64 |  |
| 7 | 2.1*25 | 10 | Load | 61.52 | 2.45 | 69 |
|  |  |  | EP | 97.66 | 0.57 |  |
| 8 | 2.1*25 | 8.55 | Load | 61.64 | 2.68 | 71 |
|  |  |  | EP | 98.07 | 0.48 |  |
| 9 | 5*25 | 9.14 | Load | 60.97 | 3.81 | 71 |
|  |  |  | EP | 96.98 | 0.70 |  |
| 10 | 5*25 | 11.28 | Load | 60.97 | 3.81 | 74 |
|  |  |  | EP | 96.69 | 0.68 |  |

The reminiscent glycosylated impurities are eliminated using a second reverse phase purification step employing high pH to increase the insulin glargine purity to >99.5%.

Example 2 illustrates purification step-2 which is Reverse phase purification-2 at high pH via experiment no 11 to 20.

Experiment 11

The reverse phase purification-1 end containing human insulin glargine in the concentration of 2.8 mg/ml and ~29% acetonitrile, was adjusted to pH 8.5 with 2M Tris and diluted with purified water to obtain a final insulin glargine concentration of 1.3 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~6.5 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 14.

TABLE 14

Results of Experiment 11

| Loading(g/L) | Stage | % Purity | % Total glycosylated variants | % Recovery |
|---|---|---|---|---|
| 6.58 | Load | 96.54 | 0.44 | 93 |
|  | EP | 99.93 | BLOD |  |

Experiment 12

The reverse phase purification-1 end containing human insulin glargine in the concentration of 2.8 mg/ml and ~29% acetonitrile, was adjusted to pH 8.5 with 2M Tris and diluted with purified water to obtain a final insulin glargine concentration of 1.3 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~6.6 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 15.

TABLE 15

Results of Experiment 12

| Loading(g/L) | Stage | % Purity | % Total glycosylated variants | % Recovery |
|---|---|---|---|---|
| 6.62 | Load | 96.85 | 0.44 | 89 |
|  | EP | 99.94 | BLOD |  |

Experiment 13

The reverse phase purification-1 end containing human insulin glargine in the concentration of 2.8 mg/ml and ~29% acetonitrile, was adjusted to pH 8.5 with 2M Tris and diluted with purified water to obtain a final insulin glargine concentration of 1 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~9 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 16.

TABLE 16

Results of Experiment 13

| Loading(g/L) | Stage | % Purity | % Total glycosylated variants | % Recovery |
|---|---|---|---|---|
| 8.95 | Load | 96.55 | 0.95 | 80 |
|  | EP | 99.88 | BLOD |  |

Experiment 14

The reverse phase purification-1 end containing human insulin glargine in the concentration of 2.9 mg/ml and ~29% acetonitrile, was adjusted to pH 8.5 with 2M Tris and diluted with purified water to obtain a final insulin glargine concentration of 1 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~9 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 17.

TABLE 17

Results of Experiment 14

| Loading (g/L) | Stage | % Purity | % Total glycosylated variants | % Recovery |
|---|---|---|---|---|
| 8.95 | Load | 96.94 | 0.63 | 83 |
|  | EP | 99.96 | BLOD |  |

Experiment 15

The reverse phase purification-1 end containing human insulin glargine in the concentration of 3.8 mg/ml and ~29% acetonitrile, was adjusted to pH 8.5 with 2M Tris and diluted with purified water to obtain a final insulin glargine concentration of 0.5 mg/ml with 10% acetonitrile, to be used as the load sample. A pre-packed, reverse phase Kromasil 100-13-C8 column (1*25 cm) was used to purify insulin glargine. The column was initially equilibrated with 90% of 00 OmM Tris+50 mM sodium perchlorate buffer at pH 8.5±0.1 and 10% Acetonitrile for 5 column volumes. The sample was loaded onto the column at a binding capacity of ~7 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 18.

TABLE 18

Results of Experiment 15

| Loading(g/L) | Stage | % Purity | % Total glycosylated variants | % Recovery |
|---|---|---|---|---|
| 6.75 | Load | 96.85 | 0.67 | 92 |
|  | EP | 99.89 | BLOD |  |

Experiment 16

The reverse phase purification-1 end containing human insulin glargine in the concentration of 3.8 mg/ml and ~29% acetonitrile, was adjusted to pH 8.5 with 2M Tris and diluted with purified water to obtain a final insulin glargine concentration of 1.2 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~6 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 19.

TABLE 19

Results of Experiment 16

| Loading(g/L) | Stage | % Purity | % Total glycosylated variants | % Recovery |
|---|---|---|---|---|
| 6.35 | Load | 96.74 | 0.58 | 84 |
|  | EP | 99.85 | BLOD |  |

Experiment 17

The reverse phase purification-1 end containing human insulin glargine in the concentration of 3.4 mg/ml and ~29% acetonitrile, was adjusted to pH 8.5 with 2M Tris and diluted with purified water to obtain a final insulin glargine concentration of 1.2 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~4 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 20.

TABLE 20

Results of Experiment 17

| Loading(g/L) | Stage | % Purity | % Total glycosylated variants | % Recovery |
|---|---|---|---|---|
| 3.88 | Load | 96.94 | 0.62 | 80 |
|  | EP | 99.95 | BLOD |  |

Experiment 18

The reverse phase purification-1 end containing human insulin glargine in the concentration of 4.2 mg/ml and ~29% acetonitrile, was adjusted to pH 8.5 with 2M Tris and diluted with purified water to obtain a final insulin glargine concentration of 1.5 mg/ml with 10% acetonitrile, to be used as the load sample. A pre-packed, reverse phase Kromasil 100-13-C8 column (2.1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~6 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 21.

TABLE 21

Results of Experiment 18

| Loading(g/L) | Stage | % Purity | % Total glycosylated variants | % Recovery |
| --- | --- | --- | --- | --- |
| 5.85 | Load | 97.78 | 0.43 | 78 |
|  | EP | 99.89 | BLOD |  |

Experiment 19

The reverse phase purification-1 end containing human insulin glargine in the concentration of 4.2 mg/ml and 29% acetonitrile, was adjusted to pH 8.5 with 2M Tris and diluted with purified water to obtain a final insulin glargine concentration of 1.5 mg/ml with 10% acetonitrile, to be used as the load sample. A pre-packed, reverse phase Kromasil 100-13-C8 column (2.1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~9 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 22.

TABLE 22

Results of Experiment 19

| Loading(g/L) | Stage | % Purity | % Total glycosylated variants | % Recovery |
| --- | --- | --- | --- | --- |
| 8.73 | Load | 96.69 | 0.65 | 83 |
|  | EP | 99.94 | BLOD |  |

Experiment 20

The reverse phase purification-1 end containing human insulin glargine in the concentration of 4.5 mg/ml and 29% acetonitrile, was adjusted to pH 8.5 with 2M Tris and diluted with purified water to obtain a final insulin glargine concentration of 1.8 mg/ml with 10% acetonitrile, to be used as the load sample. A pre-packed, reverse phase Kromasil 100-13-C8 column (2.1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~8 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-29% Acetonitrile with 100 mM Tris+50 mM sodium perchlorate buffer at pH 8.5±0.1 over 25 column volumes. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated below table 23.

TABLE 23

Results of Experiment 20

| Loading(g/L) | Stage | % Purity | % Total glycosylated variants | % Recovery |
| --- | --- | --- | --- | --- |
| 8.05 | Load | 97.04 | 0.57 | 76 |
|  | EP | 99.94 | BLOD |  |

The summary of experimental data of Reverse phase purification-2 at high pH is elaborated below in table 24.

The second reverse phase purification step for insulin Glargine used high pH buffers coupled with ion pairing agent sodium perchlorate to reduce the reminiscent glycosylated variants to below detection levels, thereby increasing the purity from >96% in the load to >99.5% in the elution pool.

TABLE 24

Summary of experimental data of Reverse phase purification-2 at high pH

| Experiment No. | Column ID(mm) | Loading (g/L) | Stage | % Purity | % Total glycosylated variants | % Recovery |
| --- | --- | --- | --- | --- | --- | --- |
| 11 | 1*25 | 6.58 | Load | 96.54 | 0.44 | 93 |
|  |  |  | EP | 99.93 | BLOD |  |
| 12 | 1*25 | 6.62 | Load | 96.85 | 0.44 | 89 |
|  |  |  | EP | 99.94 | BLOD |  |
| 13 | 1*25 | 8.95 | Load | 96.55 | 0.95 | 80 |
|  |  |  | EP | 99.88 | BLOD |  |
| 14 | 1*25 | 9.12 | Load | 96.94 | 0.63 | 83 |
|  |  |  | EP | 99.96 | BLOD |  |

TABLE 24-continued

Summary of experimental data of Reverse phase purification-2 at high pH

| Experiment No. | Column ID(mm) | Loading (g/L) | Stage | % Purity | % Total glycosylated variants | % Recovery |
|---|---|---|---|---|---|---|
| 15 | 1*25 | 6.75 | Load | 96.85 | 0.67 | 92 |
|  |  |  | EP | 99.89 | BLOD |  |
| 16 | 1*25 | 6.35 | Load | 96.74 | 0.58 | 84 |
|  |  |  | EP | 99.85 | BLOD |  |
| 17 | 1*25 | 3.88 | Load | 96.94 | 0.62 | 80 |
|  |  |  | EP | 99.95 | BLOD |  |
| 18 | 2.1*25 | 5.85 | Load | 97.78 | 0.43 | 78 |
|  |  |  | EP | 99.89 | BLOD |  |
| 19 | 2.1*25 | 8.27 | Load | 96.69 | 0.65 | 83 |
|  |  |  | EP | 99.94 | BLOD |  |
| 20 | 5*25 | 8.05 | Load | 97.04 | 0.57 | 76 |
|  |  |  | EP | 99.94 | BLOD |  |

Note:
LOQ for the analytical method is 0.04% and LOD is 0.02%

Figure 3A:
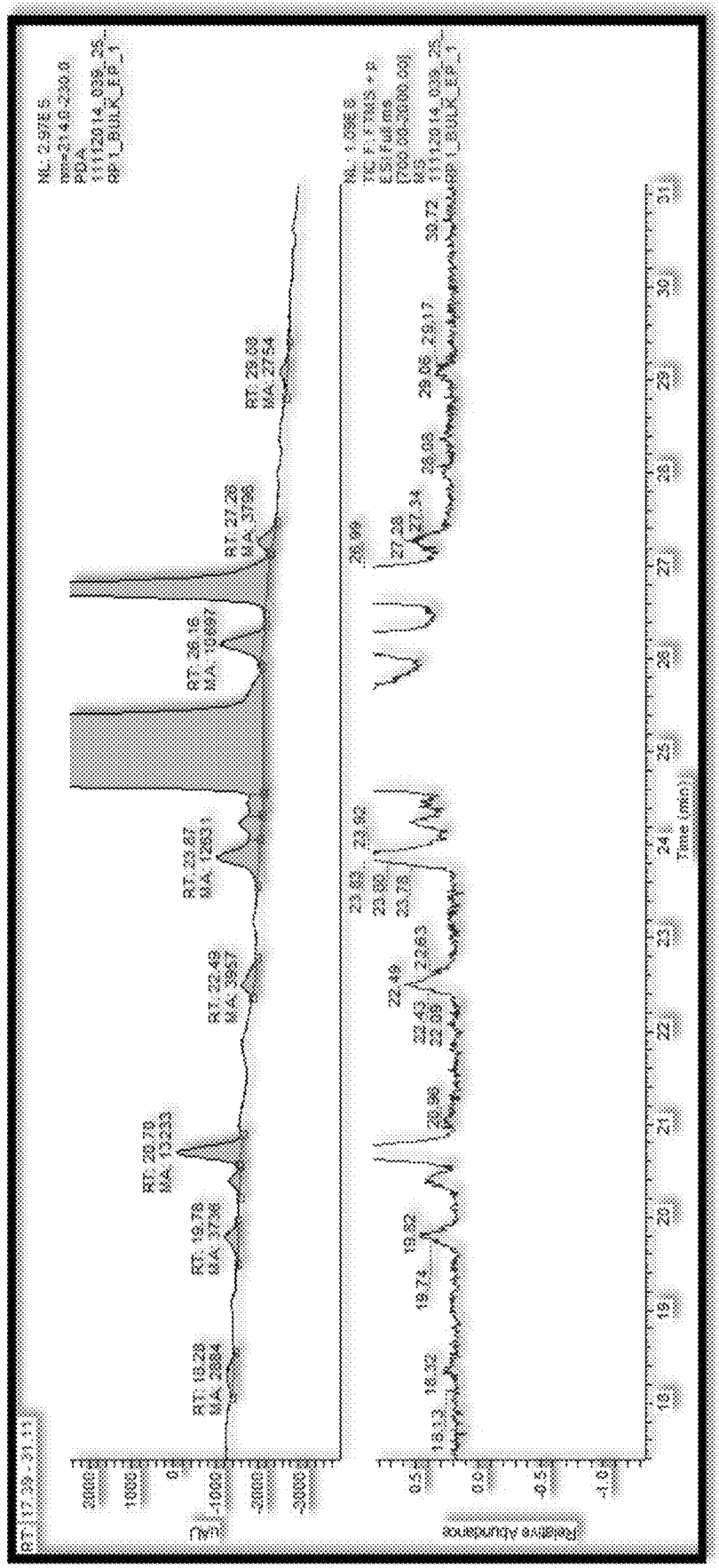
FIG. 3A represents UV and TIC chromatogram Reverse phase purification-1 end of process of purification of insulin glargine with low pH followed by high pH chromatography.
Figure 3B:
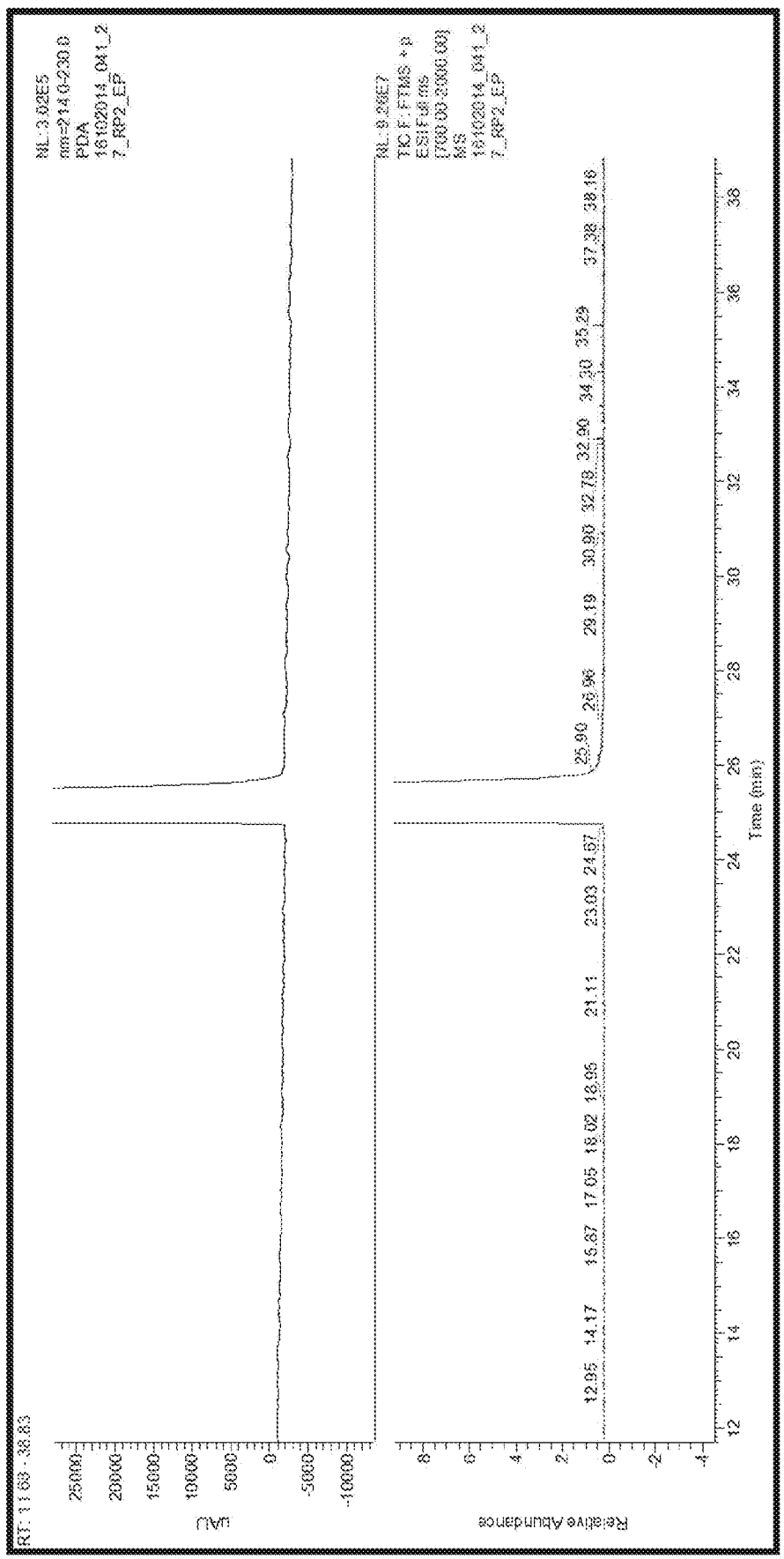
FIG. 3B represents UV and TIC chromatogram Reverse phase purification-2 end of process of purification of insulin glargine with low pH followed by high pH chromatography.

Quality profile and Probable mass based ID by end of reverse phase purification step 1 and 2 are as elaborated below in table 25 and 26 respectively. The Mass spectrometry data UV and TIC chromatogram at Reverse phase purification-1 end and Reverse phase purification-2 end was as per FIG. 3A and FIG. 3B respectively.

TABLE 25

Quality profile of glycoforms and probable mass based ID by end of reverse phase purification step-1.

| RRT | Levels observed in C18 HPLC method (%) at RP purification-1 load | Levels observed in C18 HPLC method (%) at RP purification-1 elution pool | Probable Mass based Identity |
|---|---|---|---|
| 0.80 | 0.32 | 0.06 | Diglycosylated insulin glargine |
| 0.82 | 0.66 | 0.04 | Monoglycosylated insulin glargine, Diglycosylated insulin glargine |
| 0.84 |  | 0.20 | Monoglycosylated insulin glargine |
| 0.96 | 0.61 | 0.19 | Insulin glargine + 16 Da, Monoribosylated insulin glargine, Diglycosylated insulin glargine, Hydrolysed IG with Leader |
| 0.99 | 0.62 | 0.08 | Insulin glargine + 16 Da, Monoglycosylated insulin glargine |
| 1.00 | 62.47 | 97.64 | Insulin Glargine |

TABLE 26

Quality profile and Probable mass based ID by end of reverse phase purification step- 2.

| RT | Levels observed in C18 HPLC method at RP purification-2 elution pool | Probable Mass based ID |
|---|---|---|
| 0.84 | BLOD, No charge support, No Isotopic distribution | Monoglycosylated insulin glargine |
| 0.92 | BLOD | 6094.8 Da |
| 0.99 | BLOD, No charge support, No Isotopic distribution | Monoglycosylated insulin glargine |
| 1.00 | BLOD, No charge support, No Isotopic distribution | Insulin Glargine |

Purification of Insulin Lispro Wherein Low pH Based RP-HPLC is Followed by High pH Based RP-HPLC The Purification step-1 at low pH was as shown in flowchart of FIG. 1. The details of purification step-1 were as follows Stationary phase details:
  d. Media: Daisopak C18-200A-10 pm
  e. Height: 25. Oil. 0 cm
  f. Linear velocity: <360 cm/h for all the chromatographic steps.

Mobile phase details:
  d. Mobile phase A: 400 mM Tri-sodium citrate-citric acid buffer+0.1% (w/v) Octane sulphonic acid (OSA)+50 mM GuCI (Guanidinium chloride) at pH 3.85±0.1.
  e. Mobile phase B: 100.0% Acetonitrile
  f. Mobile phase A & B temperature during purification cycle: 25-30° C.

Load preparation:
  e. Load concentrate obtained from the preceding step was diluted with a mixture of purified water and acetic acid at the ratio of >1.0:10.0.
  f. After dilution, the sample was filtered through 1.2 pm, 0.45 pm followed by 0.22 pm filters.
  g. Filters used for 1.2 pm filtration was made of polypropylene (PP) & for 0.45/0.22 pm filtration was made of polyether sulfone (PES) material.
  h. The product concentration in the load was in the range of 1.0 to 2.0 g/L.

Process conditions for purification:
  h. The column was equilibrated for 5-10 CVs (column volumes) using mobile phase of 90.0% (A):10.0% (B) at linear velocity of <360 cm/h.

i. The column was loaded at a capacity of 5-7.5 g lispro/L of resin at linear velocity of <360 cm/h.

j. After loading, the column was washed for 4-5 CVs (column volumes) using mobile phase of 78.0% (A): 22.0% (B) at linear velocity of <360 cm/h.

k. The product was eluted out from the column using linear gradient of 24-28% B over 20 CVs at linear velocity of <220 cm/h·L. During elution, variable volume fraction collection was performed based on rise in absorbance (UV) at 280 nm. The collection was continued till UV280 drops to baseline. The volume required to elute the protein from the column was 2.0-3.0 CVs.

m. The elution fractions were analyzed and pooled based on their purity levels and the prepared elution pool was stored at 2-8° C.

n. After elution to remove the residual protein if any, the column was regenerated for 2 CVs in the up-flow direction using 50.0% 1M acetic acid & 50.0% acetonitrile, followed by 1 CV using 30.0% 1M acetic acid & 70.0% acetonitrile at linear velocity of <360 cm/h.

Results tabulated data in table 27. According to data, the glycosylated proteins were reduced by ~3 folds i.e. from ~4% in the load to ~1.0% in the elution pool (EP).

TABLE 27

Results of purification step-1 at low pH

| Trial No. | Stage | % Purity of insulin Lispro 1.00 RRT | % Purity of glycosylated insulin lispro | | | % Recovery |
| --- | --- | --- | --- | --- | --- | --- |
| | | | 0.81 RRT | 0.93 RRT | 0.97 RRT | |
| 1. | Load | 63.91 | 1.55 | 3.22 | 0.41 | 30.76 |
| | EP | 91.11 | BLOD | 0.16 | 0.00 | |
| 2. | Load | 60.76 | 1.03 | 1.85 | 0.77 | 32.69 |
| | EP | 84.31 | 0.14 | 0.12 | 0.00 | |
| 3. | Load | 62.07 | 0.87 | 1.66 | 0.39 | 25.29 |
| | EP | 85.68 | 0.28 | BLOD | 0.38 | |
| 4. | Load | 58.96 | 1.41 | 1.67 | 0.81 | 27.71 |
| | EP | 85.44 | 0.09 | 0.42 | 0.51 | |

Note:
LOQ for the analytical method is 0.05% and LOD is 0.03%

The elution pool from purification step-1 was subjected to purification step-2 for further purification of the non-glycosylated proteins from the glycosylated proteins.

The Purification step-2 at high pH were as shown in flowchart of FIG. 2. The details of purification step-2 were as follows Stationary phase details:

a. Media: Phenomenex C8-100A-10 pm b. Height: 25. Oil. 0 cm c. Linear velocity: <360 cm/h for all the chromatographic steps Mobile phase details:

a. Mobile phase A: 100 mM Tris+50 mM Imidazole+0.2% (w/v) Tetra butyl ammonium bisulphate (TBAB) at pH 7.5±0.1 (pH is adjusted using Glacial acetic acid)

b. Mobile phase B: 100.0% Acetonitrile c. Mobile phase A& B temperature during purification cycle: 26-30° C.

Load preparation:

a. Elution pool (EP) obtained from purification step-1 was diluted with purified water in the ratio of 1.0:2.0.

b. Diluted sample pH was adjusted to 7.5±0.1 using 2.0M Tris.

c. After pH adjustment the sample was filtered through 1.2 pm, 0.45 pm followed by 0.22 pm.

d. Filters used for 1.2 pm filtration was made of polypropylene (PP) & for 0.45/0.22 pm filtration was made of polyether sulfone (PES) material.

e. The product concentration in the load was expected to be in the range of 1.0 to 2.0 g/L Process conditions for purification:

a. The column was equilibrated for 5-10 CVs (column volumes) using mobile phase of 90.0% (A):10.0% (B) at linear velocity of <360 cm/h.

b. The column was loaded at a capacity of 5-8.5 g lispro/L of resin at linear velocity of <360 cm/h.

c. After loading, the column was washed for 4-5 CVs (column volumes) using mobile phase of 80.0% (A): 20.0% (B) at linear velocity of <360 cm/h.

d. The product was eluted out from the column using linear gradient of 25-29% B over 13 CVs at linear velocity of <360 cm/h.

e. During elution, variable volume fraction collection was performed based on rise in absorbance (UV) at 280 nm. The collection was continued till UV drops to baseline. The volume required to elute the protein from the column was 2.0-3.0 CV.

f. The elution fractions were analyzed and, pooled based on their purity levels and the prepared elution pool was stored at 2-8° C.

g. After elution to remove the residual protein if any, the column is regenerate for 3 CVs in the up-flow direction using 50.0% purified water & 50.0% acetonitrile, followed by 30% 3M acetic acid & 70% acetonitrile at linear velocity of <360 cm/h.

Results were as per the tabulated data in table 28. According to data, the glycosylated proteins are reduced to BLOQ in the elution pool from ~0.5% in the load.

TABLE 28

Result of purification step-2 at high pH

| Trial No. | Stage | % Purity of insulin Lispro 1.00 RRT | % Purity of glycosylated Insulin Lispro | | | % Recovery |
|---|---|---|---|---|---|---|
| | | | 0.81 RRT | 0.93 RRT | 0.97 RRT | |
| 1. | Load | 86.17 | 0.19 | 0.27 | 0.00 | 39.51 |
|    | EP   | 95.25 | BLOD | BLOQ | BLOD | |
| 2. | Load | 85.14 | 0.29 | 0.39 | 0.18 | 26.59 |
|    | EP   | 96.54 | BLOD | BLOD | BLOD | |

Note:
LOQ for the analytical method is 0.05% and LOD is 0.03%; BLOQ: below level of quantification Example 3 illustrates purification step-1 which is Reverse phase purification-1 at low pH via experiment no 21 to 24. A more complete understanding can be obtained by reference to the following examples, which are provided for purposes of illustration only and are not intended to limit the scope of the disclosure.

Experiment 21

The enzyme reaction end containing human insulin lispro in the concentration of 12.7 mg/ml, was pH adjusted to <3.5 with glacial acetic acid, followed by 10% acetonitrile and diluted to 1.16 mg/ml using purified water, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI buffer at pH 3.85±0.1 and 10% Acetonitrile for around 10 column volumes. The sample was loaded onto the column at a binding capacity of ~5.6 g of human insulin lispro/L of resin. The loosely bound protein was washed with 78% 400 mM Tri-sodium citrate-citric acid buffer+ 0.1% (w/v) OSA+50 mM GuCI buffer at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI buffer at pH 3.85±0.1 over 20 column volumes at a flow rate of 220 cm/h. Multiple fractions of 0.25 column volumes were collected based on increase in absorbance at 280 nm. The tightly bound protein was eluted with 70% 3M acetic acid and 30% acetonitrile for 4 column volumes The entire unit operation except elution phase, was performed at a linear flow rate of 360 cm/h. The load sample, elution fractions and elution pool were analyzed by analytical method using C18 column manufactured by Waters. Ltd). The results are tabulated below in table 29.

TABLE 29

Results of Experiment 21

| Loading(g/L) | Stage | % Purity | % Total glycosylated variants | % Recovery |
|---|---|---|---|---|
| 5.62 | Load | 63.91 | 5.18 | 31 |
|      | EP   | 91.11 | 0.23 | |

Experiment 22

The enzyme reaction end containing human insulin lispro in the concentration of 12.7 mg/ml, was pH adjusted to <3.5 with glacial acetic acid, followed by 10% acetonitrile and diluted to 1.16 mg/ml using purified water, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI buffer at pH 3.85±0.1 and 10% Acetonitrile for around 10 column volumes. The sample was loaded onto the column at a binding capacity of ~7.4 g of human insulin lispro/L of resin. The loosely bound protein was washed with 78% 400 mM Tri-sodium citrate-citric acid buffer+ 0.1% (w/v) OSA+50 mM GuCI buffer at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI buffer at pH 3.85±0.1 over 20 column volumes at a flow rate of 220 cm/h. Multiple fractions of 0.25 column volumes were collected based on increase in absorbance at 280 nm. The tightly bound protein was eluted with 70% 3M acetic acid and 30% acetonitrile for 4 column volumes The entire unit operation except elution phase, was performed at a linear flow rate of 360 cm/h. The load sample, elution fractions and elution pool were analyzed by analytical method using C18 column manufactured by Waters Ltd). The results are tabulated below in table 30.

TABLE 30

Results of Experiment 22

| Loading(g/L) | Stage | % Purity | % Total glycosylated variants | % Recovery |
|---|---|---|---|---|
| 7.41 | Load | 60.76 | 3.65 | 33 |
|      | EP   | 84.31 | 0.26 | |

Experiment 23

The enzyme reaction end containing human insulin lispro in the concentration of 10.8 mg/ml, was pH adjusted to <3.5 with glacial acetic acid, followed by 10% acetonitrile and diluted to 1.42 mg/ml using purified water, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI buffer at pH 3.85±0.1 and 10% Acetonitrile for around 10 column volumes. The sample was loaded onto the column at a binding capacity of ~6.7 g of human insulin lispro/L of resin. The loosely bound protein was washed with 78% 400 mM Tri-sodium citrate-citric acid buffer+ 0.1% (w/v) OSA+50 mM GuCI buffer at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI buffer at pH 3.85±0.1 over 20 column volumes at a flow rate of 220 cm/h. Multiple fractions of 0.25 column volumes were collected based on increase in absorbance at 280 nm. The tightly bound protein was eluted with 70% 3M acetic acid and 30% acetonitrile for 4 column volumes The entire unit operation except elution phase, was performed at a linear flow rate of 360 cm/h. The load sample, elution fractions and elution pool were analyzed by analytical method using C18 column manufactured by Waters Ltd). The results are tabulated below in table 31.

TABLE 31

Results of Experiment 24

| Loading(g/L) | Stage | % Purity | % Total glycosylated variants | % Recovery |
|---|---|---|---|---|
| 6.76 | Load | 58.96 | 3.89 | 28 |
|  | EP | 85.44 | 0.51 |  |

The summary of experimental data of Reverse phase purification-1 at low pH is elaborated below in table 33.

TABLE 32

Summary of experimental data of Reverse phase purification-1 at low pH

| Experiment No. | Column dimensions (cm) | Loading (g/L) | Stage | % Purity | % Total glycosylated variants | % Recovery |
|---|---|---|---|---|---|---|
| 21 | 1*25 | 5.62 | Load | 63.91 | 5.18 | 31 |
|  |  |  | EP | 91.11 | 0.23 |  |
| 22 | 1*25 | 7.41 | Load | 60.76 | 3.65 | 33 |
|  |  |  | EP | 84.31 | 0.26 |  |
| 23 | 2*25 | 6.68 | Load | 62.07 | 2.92 | 25 |
|  |  |  | EP | 85.68 | 0.66 |  |
| 24 | 2*25 | 6.76 | Load | 58.96 | 3.89 | 28 |
|  |  |  | EP | 85.44 | 0.51 |  |

TABLE 31

Results of Experiment 23

| Loading(g/L) | Stage | % Purity | % Total glycosylated variants | % Recovery |
|---|---|---|---|---|
| 6.68 | Load | 62.07 | 2.92 | 25 |
|  | EP | 85.68 | 0.66 |  |

Experiment 24

The enzyme reaction end containing human insulin lispro in the concentration of 10.8 mg/ml, was pH adjusted to <3.5 with glacial acetic acid, followed by 10% acetonitrile and diluted to 1.06 mg/ml using purified water, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI buffer at pH 3.85±0.1 and 10% Acetonitrile for around 8 column volumes. The sample was loaded onto the column at a binding capacity of ~6.7 g of human insulin lispro/L of resin. The loosely bound protein was washed with 78% 400 mM Tri-sodium citrate-citric acid buffer+ 0.1% (w/v) OSA+50 mM GuCI buffer at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI buffer at pH 3.85±0.1 over 20 column volumes at a flow rate of 220 cm/h. Multiple fractions of 0.25 column volumes were collected based on increase in absorbance at 280 nm. The tightly bound protein was eluted with 70% 3M acetic acid and 30% acetonitrile for 4 column volumes The entire unit operation except elution phase, was performed at a linear flow rate of 360 cm/h. The load sample, elution fractions and elution pool were analyzed by analytical method using C18 column manufactured by Waters Ltd). The results are tabulated below in table 32.

The reverse phase purification step-1 for insulin lispro used low pH buffers coupled with ion pairing agent octane sulphonic acid (OSA) to reduce the glycosylated variants by 70-95%, thereby increasing the purity from ~58% in the load to >83% in the elution pool.

Example 4 illustrates Reverse phase purification step-2 at high pH via experiment 25 to 26.

Experiment 25

The reverse phase purification-1 end containing human insulin lispro in the concentration of 2.4 mg/ml and "'26.4% acetonitrile, was adjusted to pH 7.5 with 2M Tris and diluted with purified water to obtain a final insulin lispro concentration of 0.82 mg/ml with 10% acetonitrile, to be used as the load sample. A pre-packed, reverse phase Phenomenex 100-10-C8 column (1*25 cm) was used to purify insulin lispro. The column was initially equilibrated with 90% of 100 mM Tris+200 mM Imidazole+0.2% (w/v) TBAB buffer at pH 7.5±0.1 and 10% Acetonitrile for 10 column volumes. The sample was loaded onto the column at a binding capacity of ~8 g of human insulin lispro/L of resin. The loosely bound protein was washed with 80% 100 mM Tris+200 mM Imidazole+0.2% (w/v) TBAB buffer at pH 7.5±0.1 and 20% Acetonitrile for 4 column volumes. The bound protein were eluted at a gradient of 24-29% Acetonitrile with 100 mM Tris+200 mM Imidazole+0.2% (w/v) TBAB buffer at pH 7.5±0.1 over 13 column volumes. Multiple fractions of 0.25 column volumes were collected based on increase in absorbance at 280 nm. The tightly bound protein was eluted with 50% 100 mM Tris+200 mM Imidazole+0.2% (w/v) TBAB buffer at pH 7.5±0.1 and 50% acetonitrile for 2 column volumes, followed by 30% 3M acetic acid and 70% acetonitrile for 2 column volumes. The entire unit operation was performed at a linear flow rate of 360 cm/h. The load sample, elution fractions and elution pool were analyzed by analytical method using C18 column manufactured by Waters Ltd. The results are tabulated below table 34.

TABLE 33

Results of Experiment 25

| Loading(g/L) | Stage | % Purity | % Total glycosylated variants | % Recovery |
|---|---|---|---|---|
| 8.14 | Load | 86.17 | 0.46 | 40 |
|  | EP | 95.25 | BLOQ |  |

Experiment 26

The reverse phase purification-1 end containing human insulin lispro in the concentration of 1.3 mg/ml and ~26.4% acetonitrile, was adjusted to pH 7.5 with 2M Tris and diluted with purified water to obtain a final insulin lispro concentration of 0.5 mg/ml with 10% acetonitrile, to be used as the load sample. A pre-packed, reverse phase Phenomenex 100-10-C8 column (1*25 cm) was used to purify insulin lispro. The column was initially equilibrated with 90% of 1 mM Tris+20000 mM Imidazole+0.2% (w/v) TBAB buffer at pH 7.5±0.1 and 10% Acetonitrile for 5 column volumes. The sample was loaded onto the column at a binding capacity of "'5.6 g of human insulin lispro/L of resin. The loosely bound protein was washed with 80% 100 mM Tris+200 mM Imidazole+0.2% (w/v) TBAB buffer at pH 7.5±0.1 and 20% Acetonitrile for 4 column volumes. The bound protein were eluted at a gradient of 24-29% Acetonitrile with 100 mM Tris+200 mM Imidazole+0.2% (w/v) TBAB buffer at pH 7.5±0.1 over 13 column volumes. Multiple fractions of 0.25 column volumes were collected based on increase in absorbance at 280 nm. The tightly bound protein was eluted with 50% 100 mM Tris+200 mM Imidazole+0.2% (w/v) TBAB buffer at pH 7.5±0.1 and 50% acetonitrile for 2 column volumes, followed by 30% 3M acetic acid and 70% acetonitrile for 2 column volumes. The entire unit operation was performed at a linear flow rate of 360 cm/h. The load sample, elution fractions and elution pool were analyzed by analytical method using C18 column manufactured by Waters Ltd. The results are tabulated below table 35.

TABLE 34

Results of Experiment 26

| Loading(g/L) | Stage | % Purity | % Total glycosylated variants | % Recovery |
|---|---|---|---|---|
| 8.14 | Load | 85.14 | 0.86 | 27 |
|  | EP | 97.67 | BLOQ |  |

The summary of experimental data of Reverse phase purification-2 at high pH is elaborated below in table 35 (experiment no. 25-26).

TABLE 35

Summary of experimental data of Reverse phase purification-2 at high pH

| Experiment No. | Column ID(mm) | Loading (g/L) | Stage | % Purity | % Total glycosylated variants | % Recovery |
|---|---|---|---|---|---|---|
| 25 | 1*25 | 8.14 | Load | 86.17 | 0.46 | 40 |
|  |  |  | EP | 95.25 | BLOQ |  |
| 26 | 1*25 | 5.56 | Load | 85.14 | 0.86 | 27 |
|  |  |  | EP | 97.67 | BLOQ |  |

Note:
LOQ for the analytical method is 0.04% and LOD is 0.02%

The reverse phase purification step-2 for insulin Lispro used high pH buffers coupled with ion pairing agent tetra butyl ammonium bisulphate to reduce the reminiscent glycosylated variants to below detection levels, thereby increasing the purity from >84% in the load to >95% in the elution pool.

Quality profile and Probable mass based ID by end of reverse phase purification step-1 were as elaborated below in table 37 (experiment 21) and 38 (experiment 22) wherein Quality profile and Probable mass based ID by end of reverse phase purification step-2 were as elaborated below in table 39 (experiment 25) and 40 (experiment 26). The Mass spectrometry data UV and TIC chromatogram at Reverse phase purification-1 end was as per FIG. 4A (experiment 21) and FIG. 4B (experiment 22) and the Mass spectrometry data UV and TIC chromatogram at Reverse phase purification-2 end was as per FIG. 5A (experiment 25) and FIG. 5B (experiment 26).

TABLE 36

Figure 4A:
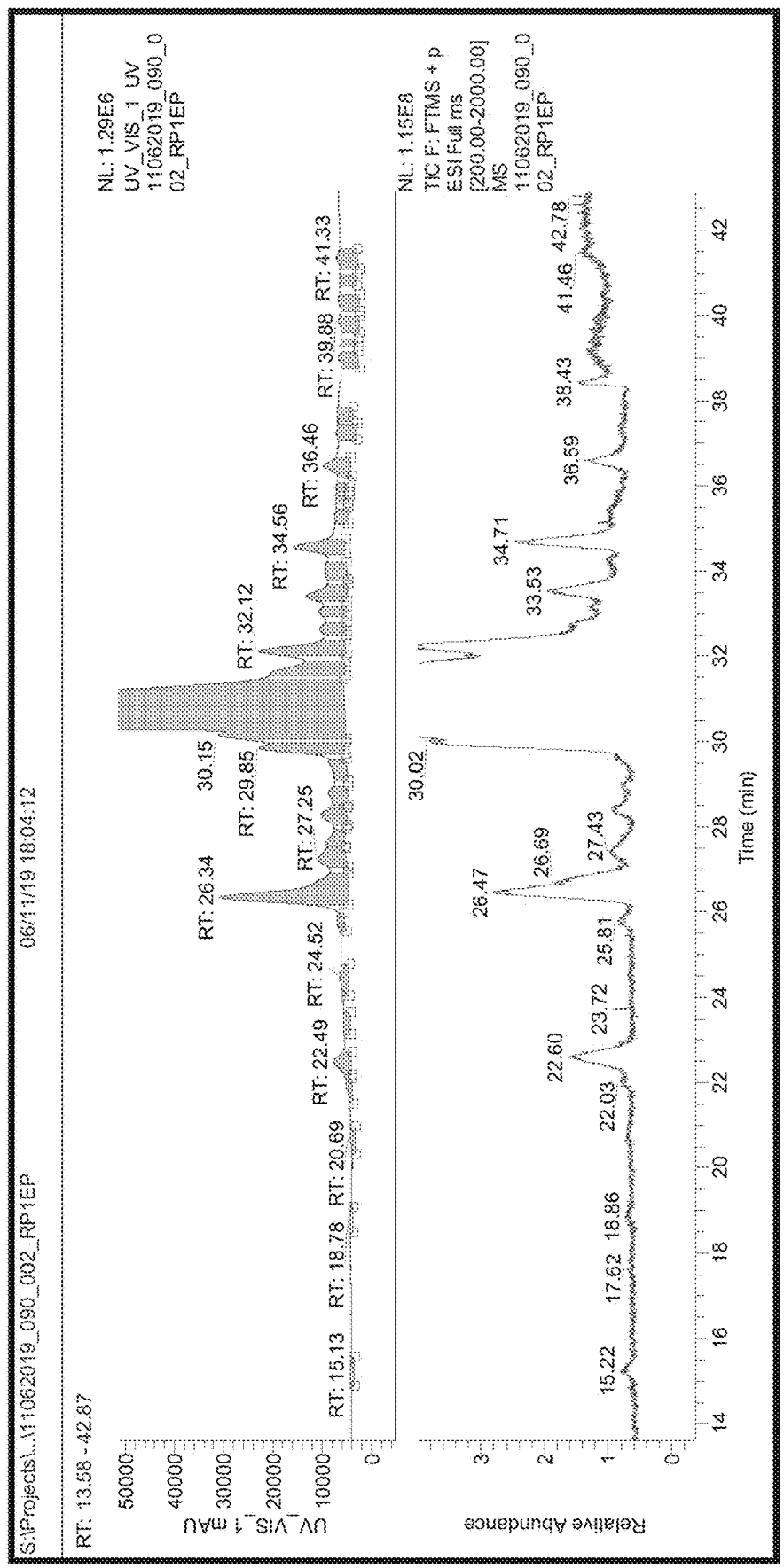
FIG. 4A, 4B represents the Mass spectrometry data-UV and TIC chromatogram at Reverse phase purification-1 end of process of purification of insulin Lispro with low pH followed by high pH chromatography.
Figure 5A:
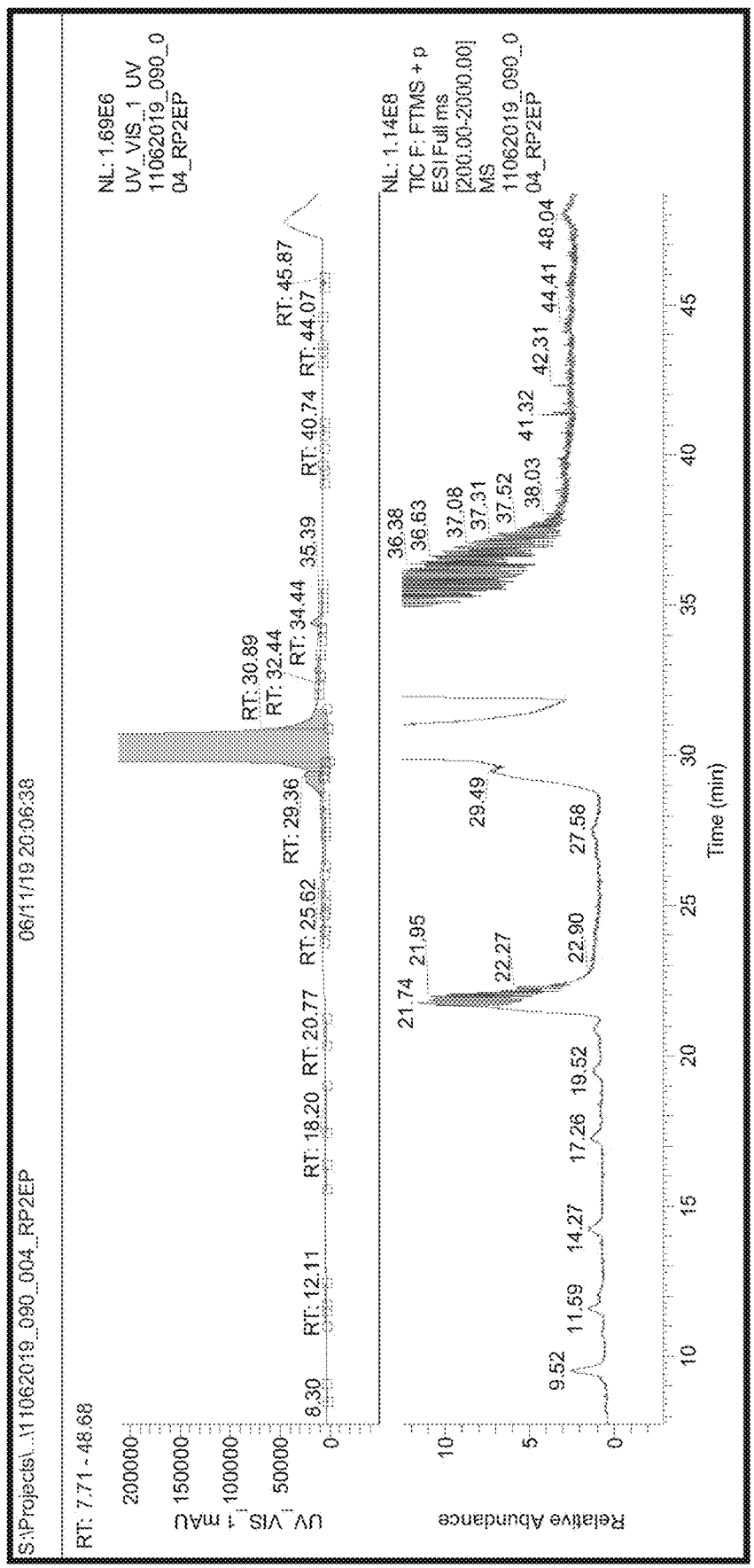
FIG. 5A, 5B represents the UV and TIC chromatogram Reverse phase purification-2 end of process of purification of insulin Lispro with low pH followed by high pH chromatography.
Figure 5B:
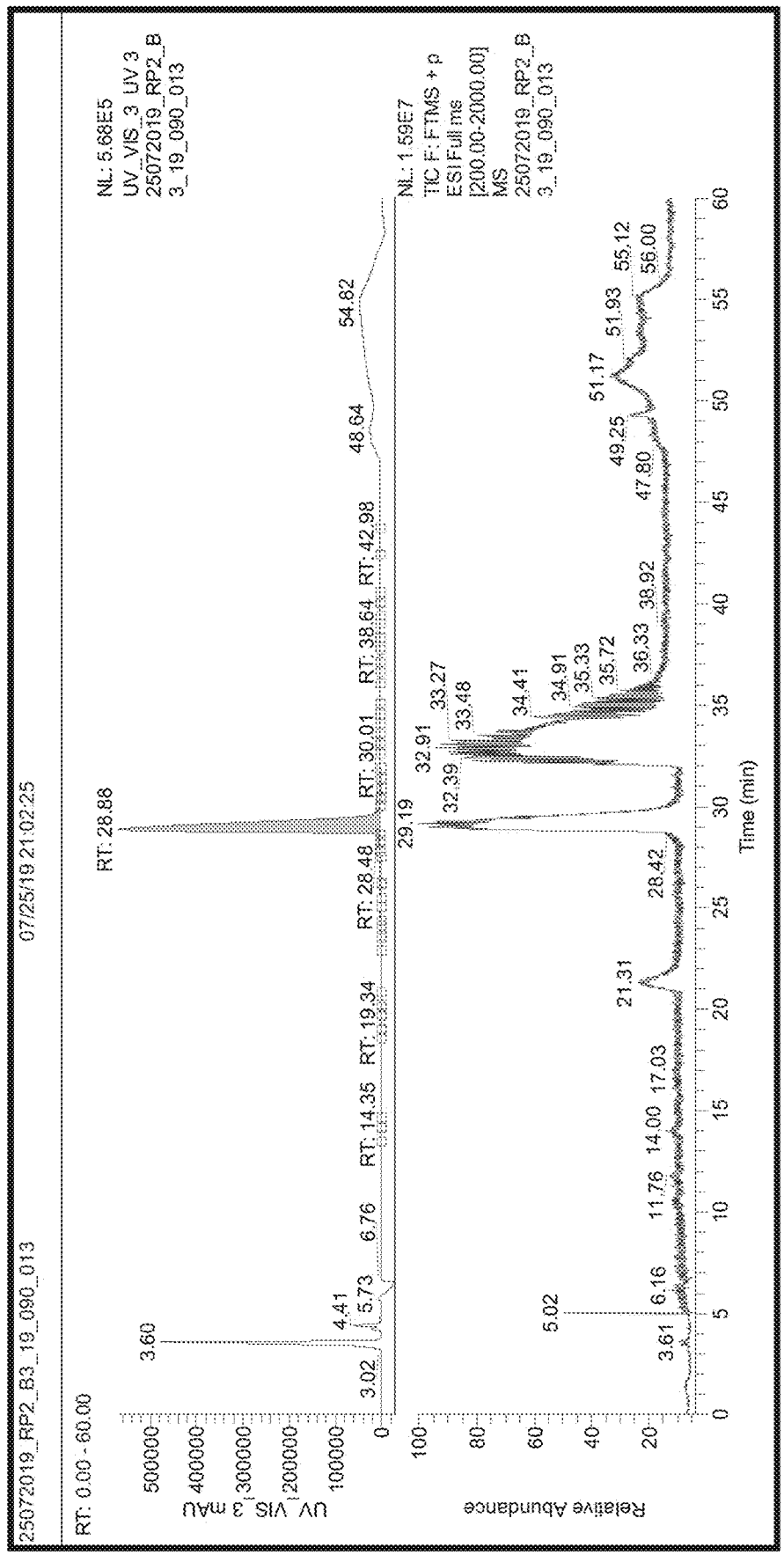

Quality profile of glycoforms and probable mass based ID by end of reverse phase purification step-1 (Experiment 21, shown in FIG. 4A)

| RRT | Levels observed in C18 HPLC method (%) at RP purification-1 elution pool | Probable Mass based Identity |
|---|---|---|
| 0.94 | 0.16 | Monoglycosylated insulin Lispro |
|  | 0.03 | Diglycosylated insulin Lispro |
| 0.97 | 0.04 | Monoglycosylated insulin Lispro |
| 1.00 | 91.11 | Insulin Lispro |

TABLE 37

Figure 4B:
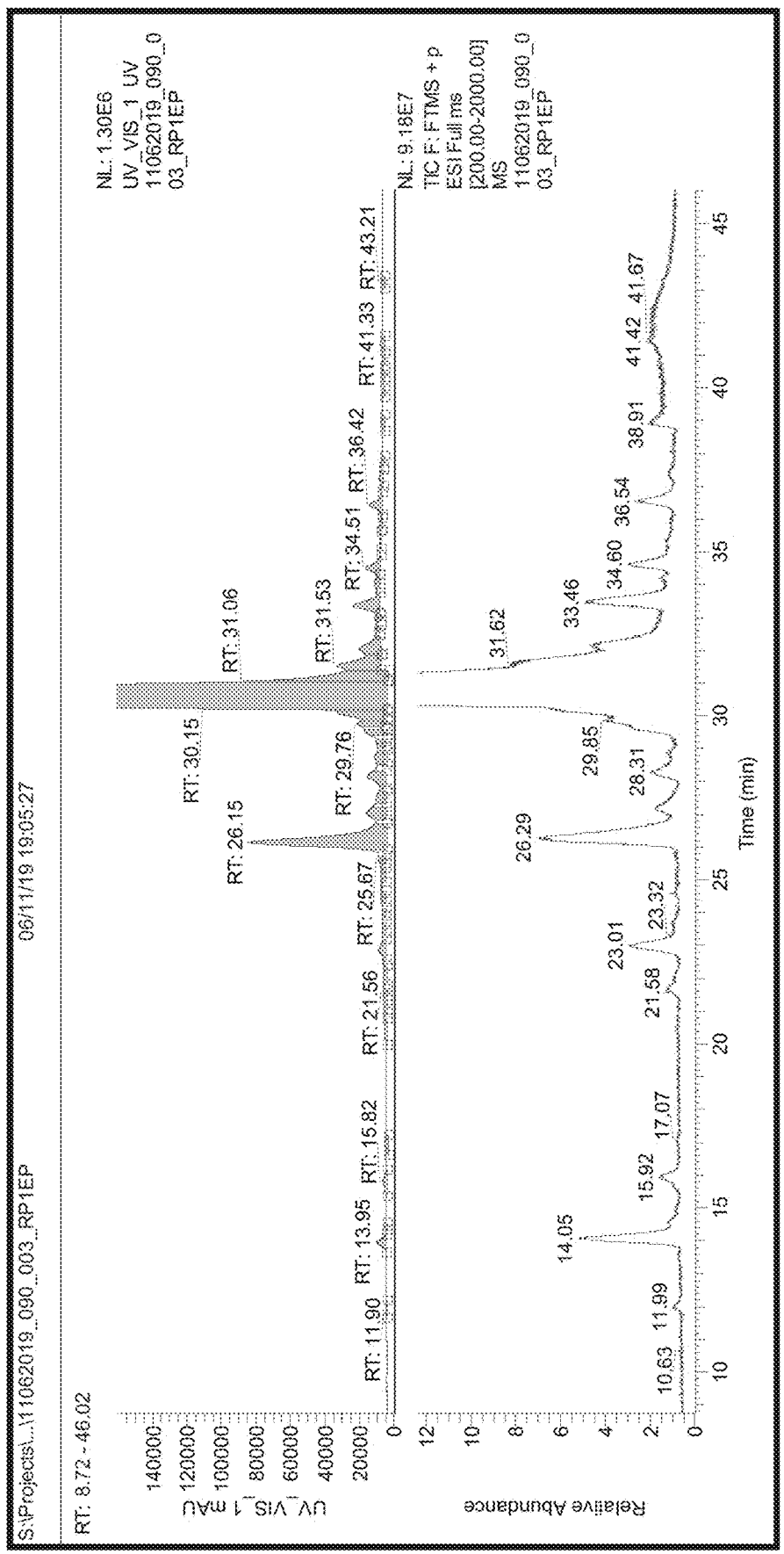

Quality profile of glycoforms and probable mass based ID by end of reverse phase purification step-1(Experiment 22, shown in FIG. 4B)

| RRT | Levels observed in C18 HPLC method (%) at RP purification-1 elution pool | Probable Mass based Identity |
|---|---|---|
| 0.81 | 0.10 | Monoglycosylated insulin Lispro |
| 0.94 | 0.12 | Monoglycosylated insulin Lispro |
| 1.00 | 84.31 | Insuln Lispro |

TABLE 38

Quality profile of glycoforms and probable mass based ID by end of reverse phase purification step-2(Experiment 25, shown in FIG. 5)

| RRT | Levels observed in C18 HPLC method (%) at RP purification-2 elution pool | Probable Mass based Identity |
|---|---|---|
| 0.92 | BLOQ | Monoglycosylated insulin Lispro |
| 0.94 | BLOD | Monoglycosylated insulin Lispro |
| 1.00 | 95.25 | Insulin Lispro |

TABLE 39

Quality profile of glycoforms and probable mass based ID by end of reverse phase purification step-2 (Experiment 26)

| RRT | Levels observed in C18 HPLC method (%) at RP purification-2 elution pool | Probable Mass based Identity |
|---|---|---|
| 0.77 | BLOQ | Monoglycosylated insulin Lispro |
| 1.00 | 97.67 | Insulin Lispro |

Purification of Insulin Glargine Wherein High pH Based RP-HPLC is Followed by Low pH Based RP-HPLC The Purification step-1 at high pH was as shown in flowchart of FIG. 1. The details of purification step-1 were as follows Stationary phase details:
  a. Media: Kromasil C8-100A-13 pm
  b. Height: 25. Oil. 0 cm
  c. Linear velocity: <360 cm/h for all the chromatographic steps Mobile phase details:
  a. Mobile phase A: 100 mM Tris+50 mM Sodium perchlorate at pH 8.5±0.1 (pH is adjusted using Glacial acetic acid)
  b. Mobile phase B: 100.0% Acetonitrile
  c. Mobile phase A& B temperature during purification cycle: 20-30° C.

Load preparation:
  a. Load concentrate obtained from the preceding step is diluted with a mixture of 0.5M Tris and 0.7M Arginine at the ratio of >1.0:10.0.
  b. Diluted sample pH was adjusted to 8.5±0.1 using Acetic acid.
  c. After pH adjustment the sample was filtered through 1.2 pm, 0.45 pm followed by 0.22 pm.
  d. Filters used for 1.2 pm filtration was made of polypropylene (PP) & for 0.45/0.22 pm filtration was made of polyether sulfone (PES) material.
  e. The product concentration in the load was expected to be in the range of 1.0 to 2.0 g/L.

Process conditions for purification:
  a. The column was equilibrated for 5-10 CVs (column volumes) using mobile phase of 90.0% (A):10.0% (B) at linear velocity of <360 cm/h.
  b. The column was loaded at a capacity of 9-10 g glargine/L of resin at linear velocity of <360 cm/h.
  c. After loading, the column was washed for 4-5 CVs (column volumes) using mobile phase of 80.0% (A): 20.0% (B) at linear velocity of <360 cm/h.
  d. The product was eluted out from the column using linear gradient of 25-30% B over 25 CVs at linear velocity of <360 cm/h.
  e. During elution, variable volume fraction collection was performed based on rise in absorbance (UV) at 280 nm. The collection was continued till UV drops to baseline. The volume required to elute the protein from the column was 2.0-3.0 CV.
  f. After fraction collection, the fractions pH was adjusted to 4.0±0.1 using glacial acetic acid. The expected acid acetic consumption was 15.0%-25.0% (V/V).
  g. The elution fractions were analyzed and pooled based on their purity levels and the prepared elution pool was stored at 2-8° C.
  h. After elution, to remove the residual protein if any, the column is regenerated for 3 CVs in the up-flow direction using 50.0% purified water & 50.0% acetonitrile at linear velocity of <360 cm/h.

Results were as per the tabulated data in table 41. According to data, the glycosylated proteins were reduced by ~9 folds i.e. from ~4.0% in the load to ~0.25% in the elution pool.

TABLE 40

Results of purification step-1 at high pH

| | | % Purity of insulin glargine | % Purity of glycosylated insulin glargine | | | | | |
|---|---|---|---|---|---|---|---|---|
| Trial No. | Stage | 1.00 RRT | 0.78-0.81 RRT | 0.82-0.84 RRT | 0.94 RRT | 0.96-0.97 RRT | 0.98-0.99 RRT | % Recovery |
| 1. | Load | 58.23 | 1.72 | 0.49 | 0.38 | 0.44 | 0.80 | 79.3 |
|  | EP | 85.15 | BLOD | BLOQ | BLOQ | BLOQ | 0.26 |  |
| 2. | Load | 56.65 | 2.01 | 0.61 | 0.46 | 0.57 | 0.62 | 84 |
|  | EP | 90.30 | BLOD | BLOD | BLOD | BLOQ | 0.28 |  |
| 3. | Load | 56.65 | 2.01 | 0.61 | 0.46 | 0.57 | 0.62 | 77.8 |
|  | EP | 90.71 | BLOD | BLOD | BLOD | BLOQ | 0.24 |  |

Note:
LOQ for the analytical method is 0.04% and LOD is 0.02%

The elution pool from purification step-1 was subjected to purification step-2 for further purification of the non-glycosylated proteins from the glycosylated proteins.

The Purification step-2 at low pH was as shown in flowchart of FIG. 2. The details of purification step-2 were as follows Stationary phase details:
  a. Media: Kromasil C8-100A-13 pm
  b. Height: 25. Oil. 0 cm c. Linear velocity: <360 cm/h for all the chromatographic steps Mobile phase details:
  a. Mobile phase A: 100 mM Sodium acetate+0.05% (w/v) Octane sulphonic acid (OSA) at pH 3.7±0.1 (pH is adjusted using Glacial acetic acid)
  b. Mobile phase B: 100.0% Acetonitrile
  c. Mobile phase A& B temperature during purification cycle: 26-30° C.

Load preparation:
  a. Elution pool obtained from the preceding step is pH adjusted to 3.7±0.1 with glacial acetic acid and diluted with purified water at the ratio of >1.0:1.5.
  b. After dilution, the sample is filtered through 1.2 pm, 0.45 pm followed by 0.22 pm filters. c. Filters used for 1.2 pm filtration is made of polypropylene (PP) & for 0.45/0.22 pm filtration is made of polyether sulfone (PES) material.
  d. The product concentration in the load expected to be in the range of 1.0 to 2.0 g/L.

Process conditions for purification:
  a. The column was equilibrated for 10 CVs (column volumes) using mobile phase of 90.0% (A):10.0% (B) at linear velocity of <360 cm/h.
  b. The column was loaded at a capacity of 6-7.5 g glargine/L of resin at linear velocity of <360 cm/h.
  c. After loading, the column was washed for 4-5 CVs (column volumes) using mobile phase of 85.0% (A): 15.0% (B) at linear velocity of <360 cm/h.
  d. The product was eluted out from the column using linear gradient of 24-31% B over 25 CVs at linear velocity of <360 cm/h.
  e. During elution, variable volume fraction collection was performed on the basis of rise in absorbance (UV) at 280 nm. The collection was continued till UV280 drops to baseline. The volume required to elute the protein from the column was 2.0-3.0 CVs.
  f. The elution fractions were analyzed and pooled based on their purity levels and the prepared elution pool was stored at 2-8° C.
  g. After elution to remove the residual protein if any, the column was regenerated for 2 CVs in the up-flow direction using 50.0% 1M acetic acid & 50.0% acetonitrile, followed by 1 CV using 30.0% 1M acetic acid & 70.0% acetonitrile at linear velocity of <360 cm/h.

Results were as per the tabulated data in table 42. According to data, the glycosylated proteins are reduced to BLOQ levels in the elution pool from ~0.3% in the load.

The elution pool from purification step-1 was subjected to purification step-2 for further purification of the non-glycosylated proteins from the glycosylated proteins.

Example 5 Illustrates Reverse phase purification-1 at high pH via experiment 27-29.

Experiment 27

The enzyme reaction end containing human insulin glargine in the concentration of 10 mg/ml, was pH adjusted to 8.5, adjusted to 10% acetonitrile, and diluted to 1.91 mg/ml using 0.5M Tris+0.7M arginine to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 10 column volumes. The sample was loaded onto the column at a binding capacity of ~9 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-30% Acetonitrile with 100 mM Tris+50 mM sodium perchlorate buffer at pH 8.5±0.1. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated in table 43:

*When purification-1 is performed at high pH, load is prepared using L-Arginine and Tris to ensure better solubility. Arginine used for load preparation does not have any influence on the purification mechanism. All other aspects of the step are kept unchanged including buffer composition and other input parameters.

TABLE 42

Results of Experiment 27

| Loading (g/l) | Stage | % Purity | % Total glycosylated variants | % Recovery |
|---|---|---|---|---|
| 9.13 | Load | 58.23 | 3.83 | 79 |
|  | EP | 83.13 | 0.46 |  |

TABLE 41

Results of purification step- 2 at low pH

| Trial No. | Stage | % Purity of insulin glargine 1.00 RRT | % Purity of glycosylated insulin glargine | | | | | % Recovery |
|---|---|---|---|---|---|---|---|---|
| | | | 0.78-0.81 RRT | 0.82-0.84 RRT | 0.94 RRT | 0.96-0.97 RRT | 0.98-0.99 RRT | |
| 1. | Load | 85.16 | BLOD | BLOD | 0.04 | 0.04 | 0.27 | 74.1 |
|  | EP | 98.64 | BLOD | BLOD | BLOD | BLOD | BLOD |  |
| 2. | Load | 91.50 | BLOQ | BLOD | 0.06 | 0.29 | 0.08 | 66.5 |
|  | EP | 98.99 | BLOD | BLOD | BLOD | BLOD | BLOD |  |
| 3. | Load | 87.32 | BLOD | BLOD | BLOD | BLOQ | 0.25 | 77.1 |
|  | EP | 98.84 | BLOD | BLOD | BLOD | BLOD | BLOD |  |

Note:
LOQ for the analytical method is 0.04% and LOD is 0.02%

Experiment 28

The enzyme reaction end containing human insulin glargine in the concentration of 10 mg/ml, was pH adjusted to 8.5, adjusted to 10% acetonitrile, and diluted to 1.91 mg/ml using 0.5M Tris+0.7M arginine* to be used as the load sample. A pre-packed, reverse phase Kromasil 100-13-C8 column (1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~9.3 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-30% Acetonitrile with 100 mM Tris+50 mM sodium perchlorate buffer at pH 8.5±0.1. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated in table 44:

*When purification-1 is performed at high pH, load is prepared using L-Arginine and Tris to ensure better solubility. Arginine used for load preparation does not have any influence on the purification mechanism. All other aspects of the step are kept unchanged including buffer composition and other input parameters.

TABLE 43

Results of Experiment 28

| Loading (g/l) | Stage | % Purity | % Total glycosylated variants | % Recovery |
|---|---|---|---|---|
| 9.36 | Load | 56.65 | 4.27 | 84 |
|  | EP | 90.30 | 0.30 |  |

Experiment 29

The enzyme reaction end containing human insulin glargine in the concentration of 10 mg/ml, was pH adjusted to 8.5, adjusted to 10% acetonitrile, and diluted to 1.91 mg/ml using 0.5M Tris+0.7M arginine* to be used as the load sample. A pre-packed, reverse phase Kromasil 100-13-C8 column (2.1*25 cm) was used to purify insulin glargine. The column was initially equilibrated with 90% of 100 mM Tris+50 mM sodium perchlorate buffer at pH 8.5±0.1 and 10% Acetonitrile for 5 column volumes. The sample was loaded onto the column at a binding capacity of ~9.75 g of human insulin glargine/L of resin. The loosely bound protein was washed with 80% 100 mM Tris+50 mM sodium perchlorate buffer at pH 8.5±0.1 and 20% Acetonitrile for 4 column volumes. The bound protein were eluted at a gradient of 25-30% Acetonitrile with 100 mM Tris+50 mM sodium perchlorate buffer at pH 8.5±0.1. Multiple fractions of 0.25 column volumes were collected based on increase in absorbance at 280 nm. The tightly bound protein was eluted with 50% purified water and 50% acetonitrile for 4 column volumes. The entire unit operation was performed at a linear flow rate of 360 cm/h. The load sample, elution fractions and elution pool were analyzed by analytical method using C18 column manufactured by YMC Co. Ltd. The results are tabulated in table 45.

*When purification-1 is performed at high pH, load is prepared using L-Arginine and Tris to ensure better solubility. Arginine used for load preparation does not have any influence on the purification mechanism. All other aspects of the step are kept unchanged including buffer composition and other input parameters.

TABLE 44

Results of Experiment 29

| Loading (g/l) | Stage | % Purity | % Total glycosylated variants | % Recovery |
|---|---|---|---|---|
| 9.75 | Load | 56.65 | 4.27 | 78 |
|  | EP | 90.71 | 0.29 |  |

The summary of experimental data of Reverse phase purification-1 at high pH is elaborated below in table 46.

TABLE 45

Summary of experimental data of Reverse phase purification-1 at high pH

| Experiment No. | Column dimensions (cm) | Loading (g/L) | Stage | % Purity | % Total glycosylated variants | % Recovery |
|---|---|---|---|---|---|---|
| 27 | 2.1*25 | 9.13 | Load | 58.23 | 3.83 | 79 |
|  |  |  | EP | 85.15 | 0.34 |  |
| 28 | 2.1*25 | 9.36 | Load | 56.65 | 4.27 | 84 |
|  |  |  | EP | 90.30 | 0.30 |  |
| 29 | 2.1*25 | 9.75 | Load | 56.65 | 4.27 | 78 |
|  |  |  | EP | 90.71 | 0.29 |  |

The first reverse phase purification step for human insulin glargine used high pH buffers coupled with ion pairing agent sodium perchlorate to reduce the glycosylated variants by 90-93%, thereby increasing the purity from ~56% in the load to >85% in the elution pool.

The reminiscent glycosylated impurities are eliminated using a second reverse phase purification step employing low pH to increase the insulin glargine purity to >99.5%.

Example 6 Illustrates Reverse phase purification step-2 at low pH via experiment 30-32.

Experiment 30

The reverse phase purification-1 end containing human insulin glargine in the concentration of "'5.06 mg/ml and "'28.8% acetonitrile, was adjusted to pH 3.7 with acetic acid and diluted with purified water to obtain a final insulin glargine concentration of ~1.69 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 10 column volumes. The sample was loaded onto the column at a binding capacity of ~6.9 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 24-31% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 47.

TABLE 46

Results of Experiment 30

| Loading (g/l) | Stage | % Purity | % Total glycosylated variants | % Recovery |
|---|---|---|---|---|
| 6.90 | Load | 85.16 | 0.35 | 74 |
|  | EP | 99.5 | BLOD |  |

Experiment 31

The reverse phase purification-1 end containing human insulin glargine in the concentration of 5.49 mg/ml and 28.8% acetonitrile, was adjusted to pH 3.7 with acetic acid and diluted with purified water to obtain a final insulin glargine concentration of 1.96 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 10 column volumes. The sample was loaded onto the column at a binding capacity of ~7.0 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 24-31% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 48.

TABLE 47

Results of Experiment 31

| Loading (g/l) | Stage | % Purity | % Total glycosylated variants | % Recovery |
|---|---|---|---|---|
| 7.06 | Load | 91.50 | 0.46 | 66 |
|  | EP | 98.99 | BLOD |  |

Experiment 32

The reverse phase purification-1 end containing human insulin glargine in the concentration of ~4.3 mg/ml and "28.6% acetonitrile, was adjusted to pH 3.7 with acetic acid and diluted with purified water to obtain a final insulin glargine concentration of ~1.5 mg/ml with 10% acetonitrile, to be used as the load sample. A pre-packed, reverse phase Kromasil 100-13-C8 column (1*25 cm) was used to purify insulin glargine. The column was initially equilibrated with 90% of 100 mM Sodium Acetate+0.05% OSA buffer at pH 3.7±0.1 and 10% Acetonitrile for around 5 column volumes. The sample was loaded onto the column at a binding capacity of ~7.5 g of human insulin glargine/L of resin. The loosely bound protein was washed with 85% 100 mM Sodium Acetate+0.05% OSA buffer at pH 3.7±0.1 and 15% Acetonitrile for around 4 column volumes. The bound protein were eluted at a gradient of 24-31% Acetonitrile with 100 mM Sodium Acetate+0.05% OSA buffer at pH 3.7±0.1. Multiple fractions of 0.25 column volumes were collected based on increase in absorbance at 280 nm. The tightly bound protein was eluted with 50% 1M acetic acid and 50% acetonitrile for 2 column volumes followed by 30% 1M acetic acid and 70% acetonitrile for 1 column volume. The entire unit operation was performed at a linear flow rate of 360 cm/h. The load sample, elution fractions and elution pool were analyzed by analytical method using C18 column manufactured by YMC Co. Ltd. The results are tabulated below in table 49.

TABLE 48

Results of Experiment 32

| Loading (g/l) | Stage | % Purity | % Total glycosylated variants | % Recovery |
|---|---|---|---|---|
| 7.51 | Load | 87.32 | 0.27 | 77 |
|  | EP | 98.84 | BLOD |  |

The summary of experimental data of Reverse phase purification-2 at low pH is elaborated below in table 50.

TABLE 49

Summary of experimental data of Reverse phase purification-2 at low pH

| Experiment No. | Column dimensions (cm) | Loading (g/L) | Stage | % Purity | % Total glycosylated variants | % Recovery |
|---|---|---|---|---|---|---|
| 30 | 1*25 | 12.1 | Load | 85.16 | 0.35 | 78 |
|  |  |  | EP | 98.64 | BLOQ |  |
| 31 | 1*25 | 12.2 | Load | 91.50 | 0.46 | 80 |
|  |  |  | EP | 98.99 | BLOQ |  |
| 32 | 1*25 | 12.2 | Load | 87.32 | 0.27 | 82 |
|  |  |  | EP | 98.84 | BLOD |  |

Note:
LOQ for the analytical method is 0.04% and LOD is 0.02%

Figure 6A:
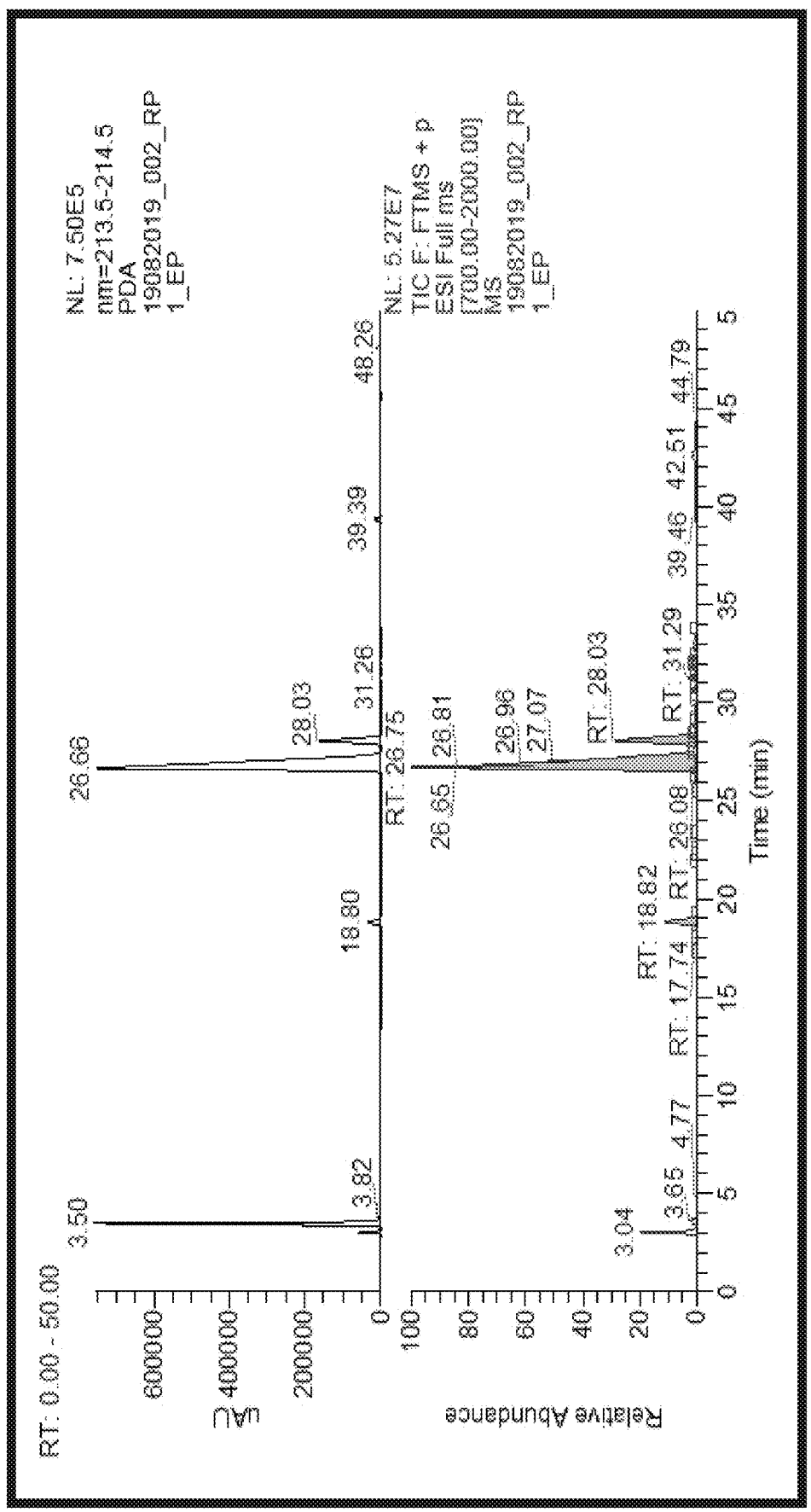
FIGS. 6A and 6B represents the mass spectrometry data of Reverse phase purification-1 and Reverse phase purification-2 end of process of purification of insulin Glargine with high pH followed by low pH chromatography.
Figure 6B:
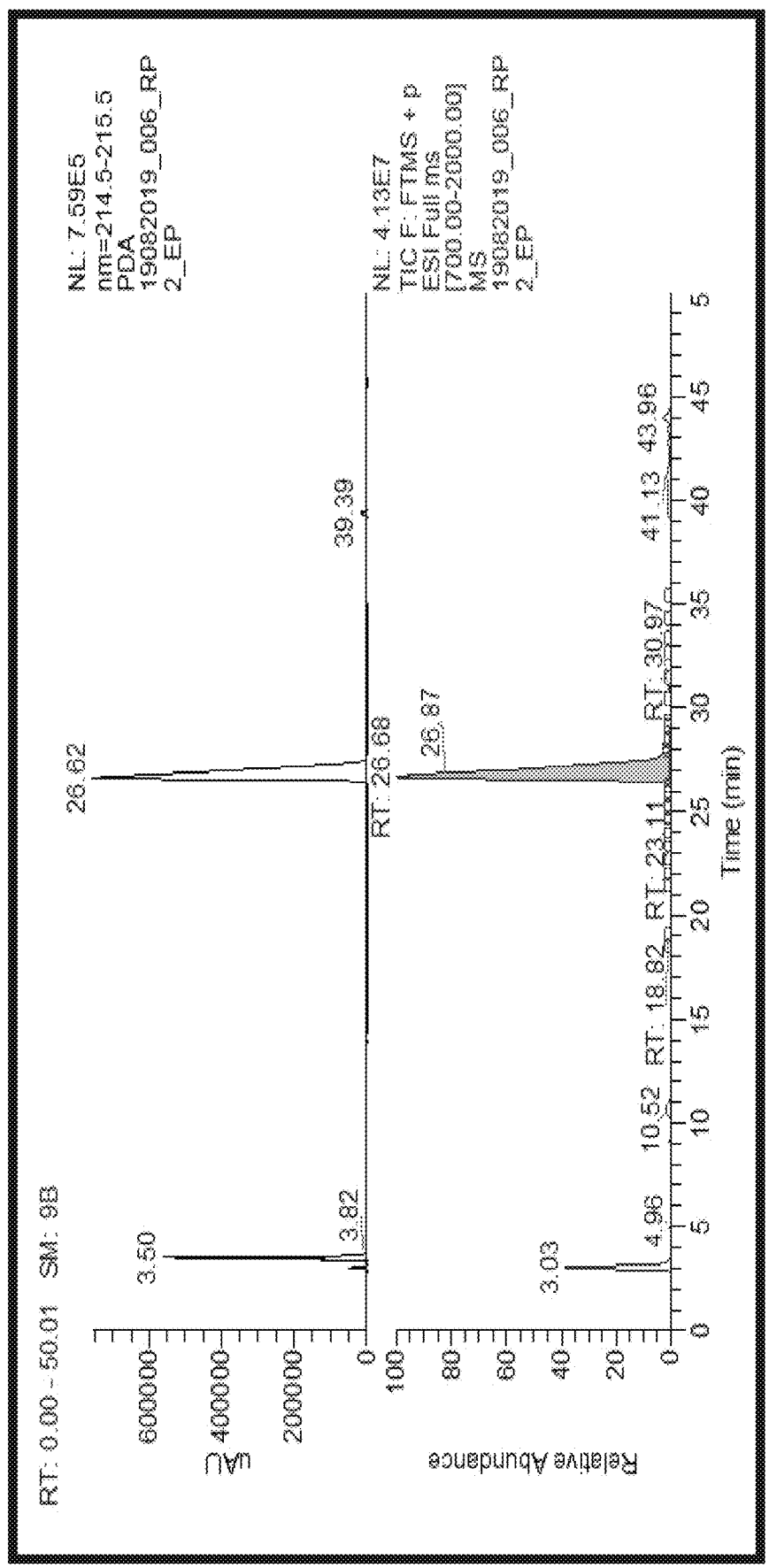

Quality profile and Probable mass based ID by end of reverse phase purification step 1 and 2 are as elaborated below in table 51 and 52 respectively. The Mass spectrometry data UV and TIC chromatogram at Reverse phase purification-1 end and Reverse phase purification-2 end was as per FIG. 6A and FIG. 6B respectively.

TABLE 51

Quality profile of glycoforms and probable mass based ID by end of reverse phase purification step -1(Experiment 27)

| RRT | Levels observed in C18 HPLC method (%) at RP purification-1 elution pool | Probable Mass based Identity |
|---|---|---|
| 0.87 | 0.10 | Monoglycosylated insulin glargine |
| 0.90 | 0.05 | Monoglycosylated insulin glargine |
| 0.98 | 0.12 | Monoglycosylated insulin glargine |
| 1.00 | 75.74 | insulin glargine |

TABLE 52

Quality profile of glycoforms and probable mass based ID by end of reverse phase purification step -2(Experiment 30)

| RRT | Levels observed in C18 HPLC method (%) at RP purification-2 elution pool | Probable Mass based Identity |
|---|---|---|
| 0.87 | BLOQ | Monoglycosylated insulin glargine |
| 0.90 | BLOQ | Monoglycosylated insulin glargine |
| 0.96 | BLOQ | Monoglycosylated insulin glargine |
| 1.00 | 99.44 | insulin glargine |

Purification of Insulin Lispro Wherein High pH Based RP-HPLC is Followed by Low pH Based RP-HPLC The Purification step-1 at high pH was as shown in flowchart of FIG. 1. The details of purification step-1 were as follows Stationary phase details:
  a. Media: Daisopak C18-200A-10 pm
  b. Height: 25. 0il. 0 cm
  c. Linear velocity: <360 cm/h for all the chromatographic steps Mobile phase details:
  a. Mobile phase A: 100 mM Tris+200 mM Imidazole+ 0.2% Tetrabutyl ammonium bisulphate (TBAB) at pH 7.5±0.1 (pH is adjusted using Glacial acetic acid)
  b. Mobile phase B: 100.0% Acetonitrile
  c. Mobile phase A& B temperature during purification cycle: 20-30° C.

Load preparation:
  a. Load concentrate obtained from the preceding step is pH adjusted to 7.5±0.1 and diluted with purified water in the ratio of >1.0:10.0.
  b. The sample was filtered through 1.2 pm, 0.45 pm followed by 0.22 pm.
  c. Filters used for 1.2 pm filtration was made of polypropylene (PP) & for 0.45/0.22 pm filtration was made of polyether sulfone (PES) material.
  d. The product concentration in the load was expected to be in the range of 1.0 to 2.0 g/L.

Process conditions for purification:
  a. The column was equilibrated for 5-10 CVs (column volumes) using mobile phase of 90.0% (A):10.0% (B) at linear velocity of <360 cm/h.
  b. The column was loaded at a capacity of 9-10 g lispro/L of resin at linear velocity of <360 cm/h.
  c. After loading, the column was washed for 4-5 CVs (column volumes) using mobile phase of 80.0% (A): 15.0% (B) at linear velocity of <360 cm/h.
  d. The product was eluted out from the column using linear gradient of 24-29% B over 13 CVs at linear velocity of <360 cm/h.
  e. During elution, variable volume fraction collection was performed on the basis of rise in absorbance (UV) at 280 nm. The collection was continued till UV drops to baseline. The volume required to elute the protein from the column was 2.0-3.0 CV.
  f. The elution fractions were analyzed and pooled based on their purity levels and the prepared elution pool was stored at 2-8° C.
  g. After elution, to remove the residual protein if any, the column is regenerated for 2 CVs in the up-flow direction using 50.0% mobile phase A and 50.0% acetonitrile, followed by 30% 3M acetic acid and 70% acetonitrile at linear velocity of <360 cm/h.

Results were as per the tabulated data in table 53. According to data, the glycosylated proteins were reduced by ~3 folds i.e. from ~4.0% in the load to ~1.0% in the elution pool.

TABLE 53

Results of purification step-1 at high pH

| Trial No. | Stage | % Purity of insulin Lispro 1.00 RRT | % Purity of glycosylated Insulin lispro | | | % Recovery |
|---|---|---|---|---|---|---|
| | | | 0.77/0.81 RRT | 0.93 RRT | 0.97/1.06 RRT | |
| 1. | Load | 58.58 | 1.41 | 1.54 | 0.54 | 73.56 |
| | EP | 85.80 | 0.78 | 1.11 | 0.07 | |
| 2. | Load | 58.58 | 1.41 | 1.54 | 0.54 | 70.44 |
| | EP | 86.88 | 0.45 | 0.92 | 0.07 | |
| 3. | Load | 58.58 | 1.41 | 1.54 | 0.54 | 64.82 |
| | EP | 85.03 | 0.60 | 2.02 | 0.06 | |

Note:
LOQfor the analytical method is 0.05% and LOD is 0.03%

The elution pool from purification step-1 was subjected to purification step-2 for further purification of the non-glycosylated proteins from the glycosylated proteins.

The Purification step-2 at low pH was as shown in flowchart of FIG. 2. The details of purification step-2 were as follows Stationary phase details:
  a. Media: Daisopak C18-200A-10 pm
  b. Height: 25. Oil. 0 cm
  c. Linear velocity: <360 cm/h for all the chromatographic steps Mobile phase details:
  a. Mobile phase A: 400 mM Tri-sodium citrate-citric acid buffer+0.1% (w/v) Octane sulphonic acid (OSA)+50 mM GuCl at pH 3.85±0.1
  b. Mobile phase B: 100.0% Acetonitrile
  c. Mobile phase A & B temperature during purification cycle: 26-30° C.

Load preparation:
  a. Elution pool obtained from the preceding step is pH adjusted to 4.0±0.1 with glacial acetic acid and diluted with purified water at the ratio of >1.0:1.5.
  b. After dilution, the sample is filtered through 1.2 pm, 0.45 pm followed by 0.22 pm filters.
  c. Filters used for 1.2 pm filtration is made of polypropylene (PP) & for 0.45/0.22 pm filtration is made of polyether sulfone (PES) material.
  d. The product concentration in the load expected to be in the range of 0.8-1.0 g/L.

Process conditions for purification:
  a. The column was equilibrated for 5-10 CVs (column volumes) using mobile phase of 90.0% (A):10.0% (B) at linear velocity of <360 cm/h.
  b. The column was loaded at a capacity of 7-8 g lispro/L of resin at linear velocity of <360 cm/h.
  c. After loading, the column was washed for 4-5 CVs (column volumes) using mobile phase of 78.0% (A): 22.0% (B) at linear velocity of <360 cm/h.
  d. The product was eluted out from the column using linear gradient of 24-28% B over 20 CVs at linear velocity of <220 cm/h.
  e. During elution, variable volume fraction collection was performed based on rise in absorbance (UV) at 280 nm. The collection was continued till UV2 so drops to baseline. The volume required to elute the protein from the column was 2.0-3.0 CVs.
  f. The elution fractions were analyzed and pooled based on their purity levels and the prepared elution pool was stored at 2-8° C.
  g. After elution to remove the residual protein if any, the column was regenerated for 4 CVs in the up-flow direction using 70.0% 1M acetic acid & 30.0% acetonitrile at a linear velocity of <360 cm/h.

Results were as per the tabulated data in table 54. According to data, the glycosylated proteins are reduced to BLOQ levels in the elution pool from ~0.3% in the load.

TABLE 54

Result of Purification step- 2 at low pH

| Trial No. | Stage | % Purity of Insulin Lispro 1.00 RRT | % Purity of glycosylated insulin lispro 0.77/0.81 RRT | 0.93 RRT | 0.97 RRT | % Recovery |
|---|---|---|---|---|---|---|
| 1. | Load | 85.95 | 0.05 | 1.10 | 0.08 | 36.20 |
|  | EP | 99.09 | BLOD | BLOQ | BLOD |  |
| 2. | Load | 85.49 | 0.07 | 0.84 | 0.08 | 43.40 |
|  | EP | 98.91 | BLOD | BLOQ | BLOD |  |
| 3. | Load | 83.37 | 0.09 | 0.83 | 0.10 | 39.40 |
|  | EP | 99.08 | BLOD | BLOQ | BLOD |  |

Note:
LOQ for the analytical method is 0.05% and LOD is 0.03%

Example 7 Illustrates Reverse phase purification step-1 at high pH via experiment 33-35.

Experiment 33

The enzyme reaction end containing human insulin lispro in the concentration of 13 mg/ml, was pH adjusted to 7.5 and 10% acetonitrile, followed by dilution to 1.45 mg/ml using purified water, to be used as the load sample. A pre-packed, reverse phase Daisopak 200-10-C18 column (2*25 cm) was used to purify insulin lispro. The column was initially equilibrated with 90% of 100 mM Tris+200 mM Imidazole+0.2% (w/v) TBAB buffer at pH 7.5±0.1 and 10% Acetonitrile for 10 column volumes. The sample was loaded onto the column at a binding capacity of ~7.3 g of human insulin lispro/L of resin. The loosely bound protein was washed with 75% 100 mM Tris+200 mM Imidazole+0.2% (w/v) TBAB buffer at pH 7.5±0.1 and 15% Acetonitrile for 4 column volumes. The bound protein were eluted at a gradient of 24-29% Acetonitrile with 100 mM Tris+200 mM Imidazole+0.2% (w/v) TBAB buffer at pH 7.5±0.1 over 13 column volumes. Multiple fractions of 0.25 column volumes were collected based on increase in absorbance at 280 nm. The tightly bound protein was eluted with 50% 100 mM Tris+200 mM Imidazole+0.2% (w/v) TBAB buffer at pH 7.5±0.1 and 50% acetonitrile for 2 column volumes, followed by 30% 3M acetic acid and 70% acetonitrile for 2 column volumes. The entire unit operation was performed at a linear flow rate of 360 cm/h. The load sample, elution fractions and elution pool were analyzed by analytical method using C18 column manufactured by Waters Ltd. The results are tabulated in table 55.

TABLE 55

Results of Experiment 33

| Loading (g/l) | Stage | % Purity | % Total glycosylated variants | % Recovery |
|---|---|---|---|---|
| 7.37 | Load | 58.58 | 3.49 | 66 |
|  | EP | 85.80 | 1.96 |  |

Experiment 34

The enzyme reaction end containing human insulin lispro in the concentration of 13 mg/ml, was pH adjusted to 7.5 and 10% acetonitrile, followed by dilution to 1.45 mg/ml using purified water, to be used as the load sample. A pre-packed, reverse phase Daisopak 200-10-C18 column (2*25 cm) was used to purify insulin lispro. The column was initially equilibrated with 90% of 100 mM Tris+200 mM Imidazole+0.2% (w/v) TBAB buffer at pH 7.5±0.1 and 10% Acetonitrile for 5 column volumes. The sample was loaded onto the column at a binding capacity of ~7.3 g of human insulin lispro/L of resin. The loosely bound protein was washed with 75% 100 mM Tris+200 mM Imidazole+0.2% (w/v) TBAB buffer at pH 7.5±0.1 and 15% Acetonitrile for 4 column volumes. The bound protein were eluted at a gradient of 24-29% Acetonitrile with 100 mM Tris+200 mM Imidazole+0.2% (w/v) TBAB buffer at pH 7.5±0.1 over 13 column volumes. Multiple fractions of 0.25 column volumes were collected based on increase in absorbance at 280 nm. The tightly bound protein was eluted with 50% 100 mM Tris+200 mM Imidazole+0.2% (w/v) TBAB buffer at pH 7.5±0.1 and 50% acetonitrile for 2 column volumes, followed by 30% 3M acetic acid and 70% acetonitrile for 2 column volumes. The entire unit operation was performed at a linear flow rate of 360 cm/h. The load sample, elution fractions and elution pool were analyzed by analytical method using C18 column manufactured by Waters Ltd. The results are tabulated in table 56.

TABLE 56

Results of Experiment 34

| Loading (g/l) | Stage | % Purity | % Total glycosylated variants | % Recovery |
|---|---|---|---|---|
| 7.37 | Load | 58.58 | 3.49 | 71 |
|  | EP | 86.88 | 1.44 |  |

Experiment 35

The enzyme reaction end containing human insulin lispro in the concentration of 13 mg/ml, was pH adjusted to 7.5 and 10% acetonitrile, followed by dilution to 1.45 mg/ml using purified water, to be used as the load sample. A pre-packed, reverse phase Daisopak 200-10-C18 column (2*25 cm) was used to purify insulin lispro. The column was initially equilibrated with 90% of 100 mM Tris+200 mM Imidazole+0.2% (w/v) TBAB buffer at pH 7.5±0.1 and 10% Acetonitrile for 5 column volumes. The sample was loaded onto the column at a binding capacity of ~7.3 g of human insulin lispro/L of resin. The loosely bound protein was washed with 75% 100 mM Tris+200 mM Imidazole+0.2% (w/v) TBAB buffer at pH 7.5±0.1 and 15% Acetonitrile for 4 column volumes. The bound protein were eluted at a gradient of 24-29% Acetonitrile with 100 mM Tris+200 mM Imidazole+0.2% (w/v) TBAB buffer at pH 7.5±0.1 over 13 column volumes. Multiple fractions of 0.25 column volumes were collected based on increase in absorbance at 280 nm. The tightly bound protein was eluted with 50% 100 mM Tris+200 mM Imidazole+0.2% (w/v) TBAB buffer at pH 7.5±0.1 and 50% acetonitrile for 2 column volumes, followed by 30% 3M acetic acid and 70% acetonitrile for 2 column volumes. The entire unit operation was performed at a linear flow rate of 360 cm/h. The load sample, elution fractions and elution pool were analyzed by analytical method using C18 column manufactured by Waters Ltd. The results are tabulated in table 57.

TABLE 57

Results of Experiment 35

| Loading (g/l) | Stage | % Purity | % Total glycosylated variants | % Recovery |
|---|---|---|---|---|
| 5.71 | Load | 58.58 | 3.49 | 65 |
|  | EP | 85.03 | 2.68 |  |

The summary of experimental data of Reverse phase purification-1 at high pH is elaborated below in table 58.

TABLE 58

Summary of experimental data of Reverse phase purification-1 at high pH

| Experiment No. | Column dimensions (cm) | Loading (g/L) | Stage | % Purity | % Total glycosylated variants | % Recovery |
|---|---|---|---|---|---|---|
| 33 | 2*25 | 7.37 | Load | 58.58 | 3.49 | 74 |
|  |  |  | EP | 85.92 | 1.19 |  |
| 34 | 2*25 | 7.37 | Load | 58.58 | 3.49 | 70 |
|  |  |  | EP | 85.36 | 1.02 |  |
| 35 | 2*25 | 5.71 | Load | 58.58 | 3.49 | 65 |
|  |  |  | EP | 83.57 | 0.96 |  |

The first reverse phase purification step for human insulin lispro used high pH buffers coupled with ion pairing agent tetra butyl ammonium bisulphate to reduce the glycosylated variants by 65-75%, thereby increasing the purity from ~58% in the load to >82% in the elution pool.

The reminiscent glycosylated impurities are eliminated using a second reverse phase purification step employing low pH to increase the insulin lispro purity to >95%.

Example 8 Illustrates Reverse phase purification step-2 at low pH via experiment 36-38.

Experiment 36

The reverse phase purification-1 end containing human insulin glargine in the concentration of "Gmg/ml and "'28.3% acetonitrile, was adjusted to pH 4.0 with acetic acid and diluted with purified water to obtain a final insulin lispro concentration of "'1.06 mg/ml with 10% acetonitrile, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI at pH 3.85±0.1 and 10% Acetonitrile for around 10 column volumes. The sample was loaded onto the column at a binding capacity of ~7.5 g of human insulin lispro/L of resin. The loosely bound protein was washed with 78% 400 mM Tri-sodium citrate-citric acid buffer+0.1% (w/v) OSA+50 mM GuCI at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI at pH 3.85±0.1 over 20 column volumes at a linear flow rate of 220 cm/h. Multiple fractions of 0.25 column volumes were collected based on increase in absorbance at 280 nm. The tightly bound protein was eluted with 30% 1M acetic acid and 70% acetonitrile for 4 column volumes. The entire unit operation except elution was performed at a linear flow rate of 360 cm/h. The load sample, elution fractions and elution pool were analyzed by analytical method using C18 column manufactured by Waters Ltd. The results are tabulated below in table 59.

TABLE 59

Results of Experiment 36

| Loading (g/l) | Stage | % Purity | % Total glycosylated variants | % Recovery |
|---|---|---|---|---|
| 7.53 | Load | 85.95 | 1.23 | 36 |
|  | EP | 99.09 | BLOQ |  |

Experiment 37

The reverse phase purification-1 end containing human insulin lispro in the concentration of ~3 mg/ml and "'28.8% acetonitrile, was adjusted to pH 4.0 with acetic acid and diluted with purified water to obtain a final insulin lispro concentration of "'1.06 mg/ml with 10% acetonitrile, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI at pH 3.85±0.1 and 10% Acetonitrile for around 10 column volumes. The sample was loaded onto the column at a binding capacity of ~7.2 g of human insulin lispro/L of resin. The loosely bound protein was washed with 78% 400 mM Tri-sodium citrate-citric acid buffer+0.1% (w/v) OSA+50 mM GuCI at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI at pH 3.85±0.1 over 20 column volumes at a linear flow rate of 220 cm/h. Multiple fractions of 0.25 column volumes were collected based on increase in absorbance at 280 nm. The tightly bound protein was eluted with 30% 1M acetic acid and 70% acetonitrile for 4 column volumes. The entire unit operation except elution was performed at a linear flow rate of 360 cm/h. The load sample, elution fractions and elution pool were analyzed by analytical method using C18 column manufactured by Waters Ltd. The results are tabulated below in table 60.

TABLE 60

Results of Experiment 37

| Loading (g/l) | Stage | % Purity | % Total glycosylated variants | % Recovery |
|---|---|---|---|---|
| 7.22 | Load | 85.49 | 0.99 | 43 |
|  | EP | 98.91 | BLOQ |  |

Experiment 38

The reverse phase purification-1 end containing human insulin lispro in the concentration of ~2.3 mg/ml and 28.6% acetonitrile, was adjusted to pH 4.0 with acetic acid and diluted with purified water to obtain a final insulin lispro concentration of ~0.83 mg/ml with 10% acetonitrile, to be used as the load sample. A pre-packed, reverse phase Daisopak 200-10-C18 column (1*25 cm) was used to purify insulin lispro. The column was initially equilibrated with 90% of 400 mM Tri-sodium citrate-citric acid buffer+0.1% (w/v) OSA+50 mM GuCI at pH 3.85±0.1 and 10% acetonitrile for around 5 column volumes. The sample was loaded onto the column at a binding capacity of ~8.0 g of human insulin lispro/L of resin. The loosely bound protein was washed with 78% 400 mM Tri-sodium citrate-citric acid buffer+0.1% (w/v) OSA+50 mM GuCI at pH 3.85±0.1 and 22% Acetonitrile for around 4 column volumes. The bound protein were eluted at a gradient of 24-28% Acetonitrile with 400 mM Tri-sodium citrate-citric acid buffer+0.1% (w/v) OSA+50 mM GuCI at pH 3.85±0.1 over 20 column volumes at a linear flow rate of 220 cm/h. Multiple fractions of 0.25 column volumes were collected based on increase in absorbance at 280 nm. The tightly bound protein was eluted with 30% 1M acetic acid and 70% acetonitrile for 4 column volumes. The entire unit operation except elution was performed at a linear flow rate of 360 cm/h. The load sample, elution fractions and elution pool were analyzed by analytical method using C18 column manufactured by Waters. Ltd. The results are tabulated below in table 61.

TABLE 61

Results of Experiment 38

| Loading (g/l) | Stage | % Purity | % Total glycosylated variants | % Recovery |
|---|---|---|---|---|
| 8.03 | Load | 83.37 | 1.02 | 39 |
|  | EP | 99.08 | BLOQ |  |

The summary of experimental data of Reverse phase purification step-2 at low pH is elaborated below in table 62.

TABLE 62

Summary of experimental data of Reverse phase purification-2 at low pH

| Experiment No. | Column dimensions (cm) | Loading (g/L) | Stage | % Purity | % Total glycosylated variants | % Recovery |
|---|---|---|---|---|---|---|
| 36 | 1*25 | 7.53 | Load | 85.95 | 1.23 | 36 |
|  |  |  | EP | 99.09 | BLOQ |  |
| 37 | 1*25 | 7.22 | Load | 85.49 | 0.99 | 43 |
|  |  |  | EP | 98.91 | BLOQ |  |
| 38 | 1*25 | 8.03 | Load | 83.37 | 1.02 | 39 |
|  |  |  | EP | 99.08 | 0 BLOQ |  |

Note:
LOQ for the analytical method is 0.05% and LOD is 0.03%

Quality profile and Probable mass based ID by end of reverse phase purification step-1 were as elaborated below in table 63 (experiment 33), table 64 (experiment 34) and table 65 (experiment 35). The quality profile and Probable mass based ID by end of reverse phase purification step-2 were as elaborated below in table 66 (experiment 36), table 67 (experiment 37) and table 68 (experiment 38). The Mass spectrometry data UV and TIC chromatogram at Reverse phase purification-1 end was as per FIG. 7A (experiment 33), FIG. 7B (experiment 34) and FIG. 7C (experiment 35). The Mass spectrometry data UV and TIC chromatogram at Reverse phase purification-2 end was as per FIG. 8A (experiment 36), 8B (experiment 37) and FIG. 8C (experiment 38).

TABLE 63

Quality profile of glycoforms and probable mass based ID by end of reverse phase purification step-1 (Experiment 33, as per FIG. 7A)

| RRT | Levels observed in C18 HPLC method (%) at RP purification-1 elution pool | Probable Mass based Identity |
|---|---|---|
| 0.77 | 0.78 | Monoglycosylated insulin Lispro |
| 0.94 | 1.11 | Monoglycosylated insulin Lispro |
| 1.00 | 85.8 | Insulin Lispro |
| 1.06 | 0.07 | Monoglycosylated insulin Lispro |

TABLE 64

Quality profile of glycoforms and probable mass based ID by end of reverse phase purification step-1 (Experiment 34, as per FIG. 7B)

| RRT | Levels observed in C18 HPLC method (%) at RP purification-1 elution pool | Probable Mass based Identity |
|---|---|---|
| 0.76 | 0.45 | Monoglycosylated insulin Lispro |
| 0.93 | 0.92 | Monoglycosylated insulin Lispro |
| 1.00 | 86.88 | Insulin Lispro |
| 1.05 | 0.07 | Monoglycosylated insulin Lispro |

TABLE 65

Quality profile of glycoforms and probable mass based ID by end of reverse phase purification step-1 (Experiment 35, as per FIG. 7C)

| RRT | Levels observed in C18 HPLC method (%) at RP purification-1 elution pool | Probable Mass based Identity |
|---|---|---|
| 0.77 | 0.48 | Monoglycosylated insulin Lispro |
| 0.77 | 0.12 | Glycosylated insulin lispro + R |
| 0.94 | 0.52 | Monoglycosylated insulin Lispro |
| 0.94 | 1.50 | Monoglycosylated insulin Lispro |
| 1.00 | 86.88 | Insulin Lispro |
| 1.05 | 0.07 | Monoglycosylated insulin Lispro |

TABLE 66

Quality profile of glycoforms and probable mass based ID by end of reverse phase purification step-2 (Experiment 36, as per FIG. 8A)

| RRT | Levels observed in C18 HPLC method (%) at RP purification-2 elution pool | Probable Mass based Identity |
|---|---|---|
| 0.94 | 0.03 | Monoglycosylated insulin Lispro |
| 1.00 | 99.09 | Insulin Lispro |

TABLE 67

Quality profile of glycoforms and probable mass based ID by end of reverse phase purification step-2 (Experiment 37, as per FIG. 8B)

| RRT | Levels observed in C18 HPLC method (%) at RP purification-2 elution pool | Probable Mass based Identity |
|---|---|---|
| 0.94 | 0.02 | Monoglycosylated insulin Lispro |
| 1.00 | 98.91 | Insulin Lispro |

TABLE 68

Quality profile of glycoforms and probable mass based ID by end of reverse phase purification step-2 (Experiment 38, as per FIG. 8C)

| RRT | Levels observed in C18 HPLC method (%) at RP purification-2 elution pool | Probable Mass based Identity |
|---|---|---|
| 0.94 | 0.03 | Monoglycosylated inuslin Lispro |
| 1.00 | 99.08 | Insulin Lispro |

CONCLUSION

As elaborated in examples, the present invention relates to a two-step purification process for the separation of non-glycosylated insulin analogues from glycosylated analogues by employing the concepts of ion pairing agent preferably OSA at one step in conjunction with alkaline pH based eluent at the other step to achieve about 99.95% removal of glycosylated forms of insulin analogues.

We claim:

1. A two step process for purification of non-glycosylated insulin analogue(s) from a complex mixture comprising both non-glycosylated, and glycosylated insulin analogue(s), wherein the said purification process comprises the steps:
   a1) performing RP-HPLC with the said complex mixture in the presence of an ion pairing agent in combination with acetonitrile as an organic modifier at acidic pH ranging from about 3.5 to about 3.9 to yield an a1 first mixture comprising partially purified non-glycosylated insulin analogue; and
   b1) performing RP-HPLC on the a1 first mixture in the presence of an ion pairing agent that is different from step a1 in combination with acetonitrile as the organic modifier at alkaline pH ranging from about 7.3 to about 8.7 to obtain at least 99.95% purified non-glycosylated insulin analogue, wherein the ion pairing agent is selected from the group consisting of octane sulphonic acid, sodium perchlorate and tetrabutyl ammonium bisulphate (TBAB);
   or;
   a2) performing RP-HPLC on said complex mixture in the presence of an ion pairing agent in combination with acetonitrile as-an organic modifier at alkaline pH ranging from about 7.3 to about 8.7 to yield an a2 first mixture comprising partially purified non-glycosylated insulin analogue; and
   b2) performing RP-HPLC with the a2 first mixture in the presence of an ion pairing agent that is different from step a2 in combination with acetonitrile as the organic modifier at acidic pH ranging from about 3.5 to about 3.9 to obtain at least 99.95% purified non-glycosylated insulin analogue, wherein the ion pairing agent is selected from the group consisting of octane sulphonic acid, sodium perchlorate and tetrabutyl ammonium bisulphate (TBAB).

2. The two step process as claimed in claim 1, wherein the insulin analogue is selected from the group consisting of insulin Glargine, and insulin Lispro.

3. The two step process as claimed in claim 1, wherein obtaining the a1 first mixture comprising partially purified non-glycosylated insulin analogue obtained by low pH-based RP-HPLC comprises the following steps:
   a) packing a RP-HPLC column with a silica-based resin;
   b) loading of the RP-HPLC column with the complex mixture at a capacity of 4-12 g/L;
   c) washing of column with an ion pairing agent in combination with acetonitrile, at acidic pH ranging from about 3.5 to about 3.9; and
   d) performing a linear gradient of 24% to 31% for eluting the a1 first mixture of partially purified non-glycosylated insulin analogue.

4. The two step process as claimed in claim 1, wherein the at least 99.95% purified non-glycosylated insulin analogue obtained by high pH-based RP-HPLC following the low pH based RP-HPLC step comprises the following steps:
   a) packing a RP-HPLC column with silica-based resin
   b) loading of the RP-HPLC column with the a1 first mixture at a capacity of 4-12 g/L;
   c) washing of column with an ion pairing agent in combination with acetonitrile at alkaline pH ranging from about 7.3 to about 8.7; and
   d) performing a linear gradient of 25% to 29% for eluting at least 99.95% purified non-glycosylated insulin analogue.

5. The two step process as claimed in claim 1, wherein obtaining the b1 first mixture comprising partially purified non-glycosylated insulin analogue is obtained by high pH-based RP-HPLC comprising the following steps:
   a) packing a RP-HPLC column with silica-based resin
   b) loading of the RP-HPLC column with the complex mixture at a capacity of 4-12 g/L;
   c) washing of the RP-HPLC column with an ion pairing agent in combination with acetonitrile at alkaline pH ranging from about 7.3 to about 8.7; and
   d) performing a linear gradient of 25% to 29% for eluting the b1 first mixture of partially purified non-glycosylated insulin analogue.

6. The two step process as claimed in claim 1, wherein the at least 99.95% purified insulin analogue is obtained by low pH-based RP-HPLC following the high pH based RP-HPLC step comprises the following steps:
   a) packing a RP-HPLC column with silica-based resin;
   b) loading of RP-HPLC column with b1 first mixture at a capacity of 4-12 g/L;
   c) washing of column with an ion pairing agent in combination with acetonitrile, at acidic pH ranging from about 3.5 to about 3.9; and
   d) performing a linear gradient of 24% to 31% for eluting at least 99.95% purified non-glycosylated insulin analogue.

7. The two step process as claimed in claim 1, wherein said ion pairing agent is sodium perchlorate when insulin analogue is insulin Glargine, and wherein said ion pairing agent is TBAB when insulin analogue is insulin Lispro.

8. The two step process as claimed in claim 1, wherein insulin analog is insulin Glargine comprising less than 0.05% glycosylated variants of insulin Glargine.

9. The two step process as claimed in claim 1, wherein insulin analog is insulin Lispro comprising less than 0.05% glycosylated variants of insulin Lispro.

10. Non-glycosylated insulin Glargine at least 99.95% free of glycosylated variants of insulin Glargine obtained according to claim 1.

11. Non-glycosylated insulin Lispro at least 99.95% free of glycosylated variants of insulin Lispro obtained according to claim 1.

12. The two step process as claimed in claim 3, wherein the insulin is glargine ion pairing agent is Octane Sulphonic Acid (OSA) and the silica-based resin is Kromasil C8-100A-13 pm.

13. The two step process as claimed in claim 4, wherein the insulin is glargine, the ion pairing agent is sodium perchlorate and the silica-based resin is Kromasil C8-100A-13 pm.

14. The two step process as claimed in claim 5, wherein the insulin is glargine, the ion pairing agent is sodium perchlorate, and the silica-based resin is Kromasil C8-100A-13 pm.

15. The two step process as claimed in claim 6, wherein the insulin is glargine, the ion pairing agent is Octane Sulphonic Acid (OSA) and the silica-based resin is Kromasil C8-100A-13 pm.

16. The two step process as claimed in claim 3, wherein the insulin is lispro, the ion pairing agent is Octane Sulphonic Acid (OSA) and the silica-based resin is Kromasil C8-100A-13 pm.

17. The two step process as claimed in claim 4, wherein the insulin is lispro, the ion pairing agent is TBAB and the silica-based resin is Kromasil C8-100A-13 pm.

18. The two step process as claimed in claim 5, wherein the insulin is lispro, the ion pairing agent is TBAB, and the silica-based resin is Kromasil C8-100A-13 pm.

19. The two step process as claimed in claim 6, wherein the insulin is lispro, the ion pairing agent is Octane Sulphonic Acid (OSA) and the silica-based resin is Kromasil C8-100A-13 pm.

20. The two step process as claimed in claim 1, wherein the purified non-glycosylated insulin analogue contains less than 0.05% of the glycosylated insulin analogue.

* * * * *